United States Patent
Kudo et al.

(10) Patent No.: US 11,033,245 B2
(45) Date of Patent: Jun. 15, 2021

(54) X-RAY CT APPARATUS AND X-RAY DETECTOR

(71) Applicant: TOSHIBA MEDICAL SYSTEMS CORPORATION, Otawara (JP)

(72) Inventors: Yoji Kudo, Otawara (JP); Masahiko Yamazaki, Utsunomiya (JP); Takashi Kanemaru, Yaita (JP); Shuya Nambu, Nasushiobara (JP); Machiko Iso, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 678 days.

(21) Appl. No.: 15/589,205

(22) Filed: May 8, 2017

(65) Prior Publication Data
US 2017/0332990 A1   Nov. 23, 2017

(30) Foreign Application Priority Data
May 19, 2016   (JP) .............................. JP2016-100316

(51) Int. Cl.
*A61B 6/00*     (2006.01)
*H04N 5/343*    (2011.01)
(Continued)

(52) U.S. Cl.
CPC ............. *A61B 6/54* (2013.01); *A61B 6/032* (2013.01); *A61B 6/4233* (2013.01); *H04N 5/32* (2013.01);
(Continued)

(58) Field of Classification Search
CPC ......... A61B 6/032; A61B 6/06; A61B 6/4233; A61B 6/5205; A61B 6/54; H04N 5/32; H04N 5/343; H04N 5/347; H04N 5/37457
See application file for complete search history.

(56) References Cited

U.S. PATENT DOCUMENTS 6,259,766 B1 *   7/2001   Cuppen .................. A61B 6/032
                                                    378/147
2008/0234571 A1 *   9/2008   Hay ........................ A61B 6/08
                                                    600/425

(Continued)

FOREIGN PATENT DOCUMENTS

JP   2008-23241 A   2/2008
JP   2009-78143     4/2009
(Continued)

OTHER PUBLICATIONS

Office Action dated Jan. 28, 2020 in Japanese Patent Application No. 2016-100316, 4 pages.
Office Action dated May 19, 2020 in Application No. 2016-100316.

*Primary Examiner* — Chih-Cheng Kao
(74) *Attorney, Agent, or Firm* — Oblon, McClelland, Maier & Neustadt, L.L.P.

(57) ABSTRACT

In one embodiment, an X-ray CT apparatus includes: an X-ray detector equipped with a plurality of detection elements each of which is configured to output an X-ray signal in accordance with X-rays passing through an object; and a scan controller configured to acquire X-ray signals in each of a first mode and a second mode in one scan by switching between the first mode and the second mode, the first mode being a mode of acquiring high-resolution data which are respective X-ray signals outputted from the plurality of detection elements, the second mode being a mode of acquiring normal-resolution data in which X-ray signals outputted from some of the plurality of detection elements are integrated.

18 Claims, 22 Drawing Sheets

(51) Int. Cl.
    *H04N 5/3745* (2011.01)
    *H04N 5/347* (2011.01)
    *H04N 5/32* (2006.01)
    *A61B 6/03* (2006.01)
    *A61B 6/06* (2006.01)

(52) U.S. Cl.
    CPC ............. *H04N 5/343* (2013.01); *H04N 5/347* (2013.01); *H04N 5/37457* (2013.01); *A61B 6/06* (2013.01); *A61B 6/5205* (2013.01)

(56) References Cited

U.S. PATENT DOCUMENTS

| | | | |
|---|---|---|---|
| 2009/0080601 A1 | 3/2009 | Tkaczyk et al. | |
| 2011/0019793 A1* | 1/2011 | Honda | A61B 6/032 378/16 |
| 2015/0110241 A1* | 4/2015 | Yamazaki | A61B 6/032 378/15 |

FOREIGN PATENT DOCUMENTS

| JP | 2010-264245 A | 11/2010 |
|---|---|---|
| JP | 2013-31674 | 2/2013 |
| JP | 2014-36871 A | 2/2014 |

\* cited by examiner

X-RAY CT APPARATUS AND X-RAY DETECTOR

CROSS-REFERENCE TO RELATED APPLICATION

This application is based upon and claims the benefit of priority from Japanese Patent Application No. 2016-100316, filed on May 19, 2016, the entire contents of which are incorporated herein by reference.

FIELD

Embodiments described herein relate generally to an X-ray CT (Computed Tomography) apparatus and an X-ray detection device.

BACKGROUND

In recent years, a high-resolution X-ray detector has been developed for an X-ray CT (Computed Tomography) apparatus, and this high-resolution X-ray detector is advantageous in that more detection elements can be arranged for unit area because each detection element is small in size. Such a high-resolution X-ray detector can acquire high-resolution data which are higher in resolution than data acquired by a conventional X-ray detector.

However, even in the case of an X-ray CT apparatus capable of acquiring high-resolution data, it is sometimes required to acquire normal resolution data (hereinafter, shortly referred to as normal data), in which resolution is reduced to approximately the same level as conventional technology, in terms of reducing image noise or interchangeability and processing speed in image processing.

For this reason, in conventional technology, there is a known method in which plural detection elements of an X-ray detector capable of acquiring high-resolution data are treated as one detection element by grouping and normal data are acquired in accordance with this grouping.

However, it is impossible in conventional technology to simultaneously acquire both of high-resolution data and normal data in one scan.

DETAILED DESCRIPTION

Hereinafter, X-ray CT apparatuses and X-ray detection devices of respective embodiments will be described by referring to the accompanying drawings.

In one embodiment, an X-ray CT apparatus includes: an X-ray detector equipped with a plurality of detection elements each of which is configured to output an X-ray signal in accordance with X-rays passing through an object; and a scan controller configured to acquire X-ray signals in each of a first mode and a second mode in one scan by switching between the first mode and the second mode, the first mode being a mode of acquiring high-resolution data which are respective X-ray signals outputted from the plurality of detection elements, the second mode being a mode of acquiring normal-resolution data in which X-ray signals outputted from some of the plurality of detection elements are integrated.

First Embodiment

Figure 1:
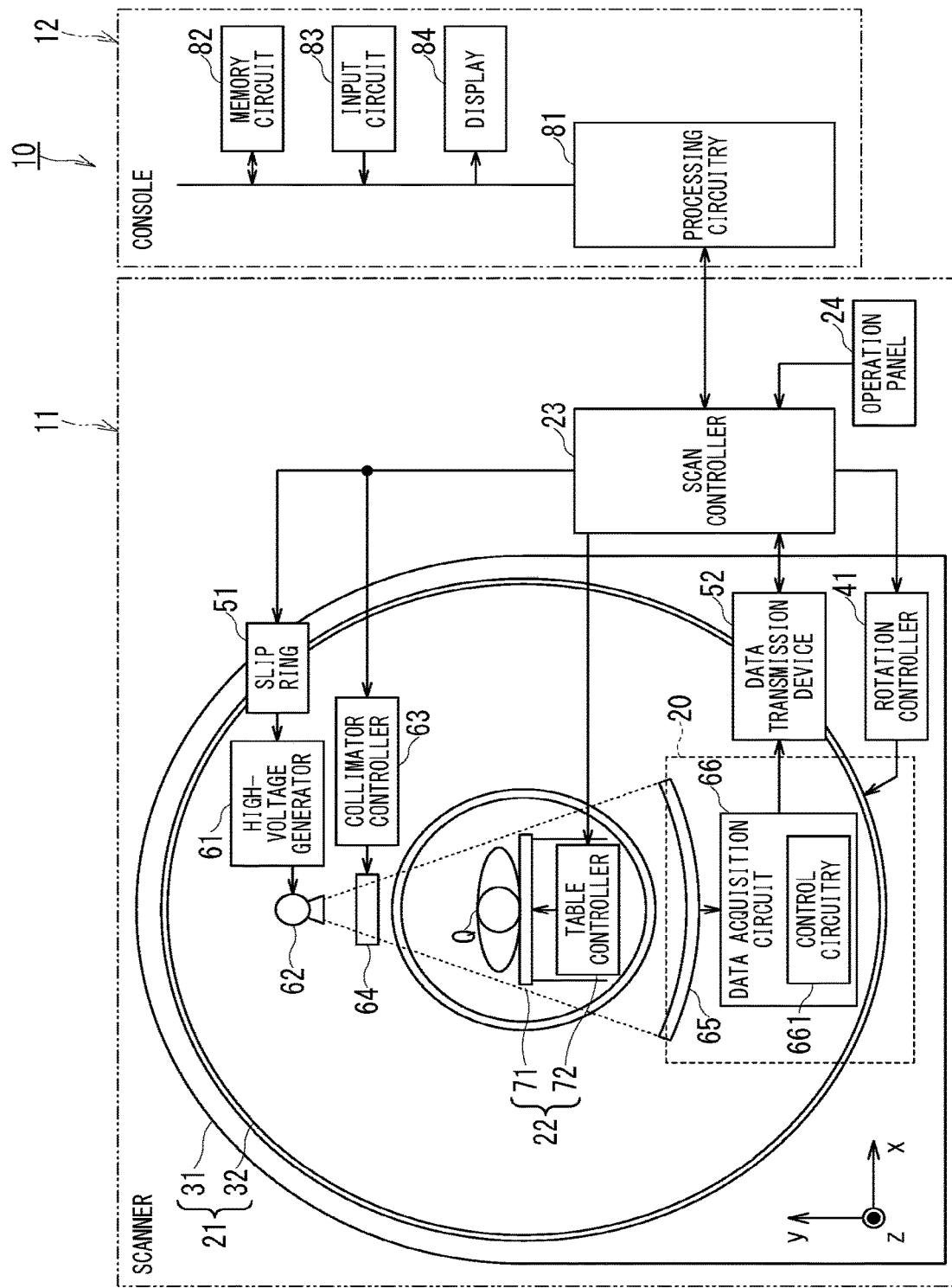
FIG. 1 is a general block diagram illustrating configuration of the X-ray CT apparatus according to the first embodiment of the present invention.

FIG. 1 is a general block diagram illustrating configuration of the X-ray CT apparatus 10 in the first embodiment. The X-ray CT apparatus 10 shown in FIG. 1 includes a scanner 11 and a console 12.

The scanner 11 is generally installed in an examination room, and generates, e.g., transmission data of X-rays related to an object Q. The console 12 is installed in a control room which is adjacent to the examination room, and performs generation and display of a reconstructed image by generating projection data on the basis of the transmission data.

The scanner 11 includes a gantry 21, a bed 22, a scan controller 23, and an operation panel 24.

The gantry 21 includes a rotating body 32 and a fixed base 31 which is fixed to a non-illustrated base. Additionally, the fixed base 31 and the rotating body 32 are covered with a non-illustrated gantry cover, and an opening is formed in the rotating body 32. The rotating body 32 is supported by a bearing such as a rolling bearing and a ball/roller bearing so as to be capable of rotating with respect to the fixed base 31.

The fixed base 31 is equipped with a rotation controller 41. The rotation controller 41 includes a non-illustrated processor and a memory, and causes the rotating body 32 to rotate with respect to the fixed base 31 in accordance with an instruction from the scan controller 23.

The fixed base 31 and the rotating body 32 include a slip ring 51 and a data transmission device 52.

The slip ring 51 is a rotating electric connector configured to keep electric conduction between the rotating body 32 and the fixed base 31 by pushing and slipping a brush against a circular circuit (i.e., metal ring), which is concentrically arranged inside the rotating body 32, from the side surface. The above-described brush is disposed on the side of the fixed base 31, and is, e.g., a carbon brush and a wire brush.

The data transmission device 52 includes a transmission circuit on the side of the rotating body 32, and further includes a reception circuit on the side of the fixed base 31. The transmission circuit transmits raw data generated by the data acquisition circuit 66 describe below to the reception circuit in a contactless manner. The reception circuit supplies the raw data transmitted from the transmission circuit to the scan controller 23 as described below.

The rotating body 32 includes a high-voltage generator 61, an X-ray tube 62, a collimator controller 63, an X-ray optical system 64, and an X-ray detection device 20. Configuration of this X-ray detection device 20 is one of the main characteristics of the X-ray CT apparatus 10 in the first embodiment. This X-ray detection device 20 includes an X-ray detector 65 and the above-described data acquisition circuit 66.

The rotating body 32 is also referred to as a rotation frame. The rotating body 32 integrally supports components such as the high-voltage generator 61 and the X-ray detection device 20 as described below. In other words, the rotating body 32 can rotate about the object Q as a whole while keeping the state in which the X-ray tube 62 and the X-ray detection device 20 face each other.

As an example here, the apparatus coordinate system of the X-ray CT apparatus 10 is defined as follows. In other words, the vertical direction is defined as the Y-axis direction, the Z-axis is defined as the direction which is perpendicular to the Y-axis direction and in parallel with the rotational axis of the rotating body 32, and the X-axis is defined as the direction which is perpendicular to those Y-axis direction and Z-axis direction.

The high-voltage generator 61 includes an AC (Alternating Current)/DC (Direct Current) converter, a DC/DC converter, and an amplifier. The AC/DC converter performs AC/DC conversion on electric power supplied from a commercial power source. The DC/DC converter converts a DC voltage into a DC voltage of a different voltage value. The amplifier generates an output current necessary for radiating X-rays of the X-ray tube 62 by using power from a DC power source. The amplifier of the high-voltage generator 61 supplies the X-ray tube 62 with electric power necessary for performing a scan in accordance with a control signal inputted from the scan controller 23 via the slip ring 51.

The X-ray tube 62 includes, e.g., a negative electrode, a rotating anode target, and a filament in its vacuum tube in the case of a rotating-anode X-ray tube. The filament produces X-rays by bombarding a metal target with an electron beam in accordance with the tube voltage supplied from the high-voltage generator 61, and radiates the produced X-rays toward the X-ray detector 65. The X-rays radiated from the X-ray tube 62 forms a fan beam of X-rays and/or a cone beam of X-rays. The X-ray tube 62 is supplied with electric power necessary for X-ray radiation under the control of the scan controller 23.

The collimator controller 63 includes a non-illustrated processor and a memory, and adjusts an irradiation range of X-rays in the slice direction of the X-ray optical system 64 under the control of the scan controller 23.

The X-ray optical system 64 is equipped with various types of control devices configured to control irradiation conditions such as dose of an X-ray beam, shape of an X-ray beam, an irradiation range, and radiation quality. Specifically, the X-ray optical system 64 is equipped with a wedge filter and a collimator. The wedge filter is formed of lightweight metal such as aluminum, and adjusts dose of X-rays generated by the X-ray tube 62. The collimator is a slit for narrowing down an irradiation range of X-rays whose dose has been controlled and adjusted by the collimator controller 63.

The X-ray detector 65 of the X-ray detection device 20 includes plural detection elements each of which detects X-rays radiated from the X-ray tube 62. The X-ray detector 65 is, e.g., a two-dimensional array type detector in which a large number of detection elements are arrayed in a matrix along the channel direction and the column direction (i.e., the slice direction). This two-dimensional array type X-ray detector 65 will be described below in detail by referring to FIG. 2.

The respective detection elements of the X-ray detector 65 detect X-rays which have been radiated from the X-ray source and have passed through an object. The X-ray detector 65 includes, e.g., a scintillator. When X-rays are radiated, X-rays colliding with this scintillator are converted into light and indirectly detected as X-ray signals by the respective detection elements.

In the case of acquiring high-resolution data, X-ray signals detected by the respective detection elements of the X-ray detector 65 are extracted, and a pixel value of one pixel is determined so as to indicate luminance level of the X-ray signal of the detection element corresponding to this one pixel. In this manner, pixel values of respective pixels of high-resolution data are determined on the basis of the X-ray signals of the respective detection elements such that respective pixels reflect the X-ray signals of the respective detection elements.

In the case of acquiring normal data, plural detection elements are treated as one detection-element group by grouping. For instance, a pixel value of one pixel of normal data is determined so as to indicate luminance level of a total value obtained by summing up respective X-ray signals of all the detection elements of one detection-element group which corresponds to this one pixel. Thus, normal data are higher in S/N ratio than high-resolution data but are lower in resolution than high-resolution data. Grouping of detection elements for acquiring normal data is performed by the scan controller 23. Grouping of detection elements will be described below in detail by referring to FIG. 3.

Incidentally, two-dimensional array type detector is also referred to as a multi-slice type detector. When the X-ray detector 65 is a multi-slice type detector, a scan of a three-dimensional region which has width in the column direction can be performed by one rotation (or a half+α rotation) of the rotating body 32. This scan is referred to as a volume scan, and voxel data, i.e., three-dimensional image data can be acquired in a volume scan.

The data acquisition circuit 66 includes control circuitry 661. The control circuitry 661 is equipped with a non-illustrated processor such as a CPU (Central Processing Unit) and a memory, and controls X-ray signals detected by the respective detection elements under the control of the scan controller 23.

The control circuitry 661 sets at least one group with respect to plural detection elements by treating plural detection elements as one detection-element group. In other words, the control circuitry 661 performs grouping of plural detection elements (e.g., divides all the detection elements into plural detection-element groups) by controlling readout of X-ray signals from the respective detection elements. The control circuitry 661 reads out a totalized X-ray signal by causing DASs (Data Acquisition Systems) of the data acquisition circuit 66 to sum up X-ray signals outputted from respective output signal lines of plural detection elements, and thereby acquires normal data in which plural detection elements are treated as one detection-element group. Further, the control circuitry 661 reads out X-ray signals outputted from respective output signal lines of plural detection elements by using the DASs corresponding to the respective detection elements so as to acquire high-resolution data.

As described above, the control circuitry 661 controls grouping of detection elements, and controls switching between the high-resolution setting (i.e., the first mode) for acquiring high-resolution data and the normal setting (i.e., the second mode) for acquiring normal data. Control of readout of X-ray signals performed by the control circuitry 661 will be described below in detail by referring to FIG. 4 to FIG. 8.

The data acquisition circuit 66 includes plural DASs. Each DAS receives an analogue signal outputted from a detection element, and performs predetermined processing such as current/voltage conversion, amplification, and A/D (Analogue/Digital) conversion on this analogue signal. The data acquisition circuit 66 generates transmission data including projection data by using X-ray signals which have been subjected to the above-described processing, and transmits the transmission data to the data transmission device 52. The transmission data transmitted to the data transmission device 52 are further transmitted to the console 12 via the scan controller 23, then are subjected to calibration such as correction of zero-order offset and/or gain adjustment, then are stored in a memory circuit 82 described below, and then are reconstructed.

The bed 22 of the scanner 11 includes a table 71 and a table controller 72. It is possible to mount the object Q on the table 71.

The table controller 72 includes a non-illustrated processor, a memory, and a motor for driving the table 71 such as a stepping motor. The table controller 72 moves the table 71 upward and downward along the Y-axis direction and horizontally moves the table 71, on which the object Q is placed, along the Z-axis direction under the control of the scan controller 23. In other words, the table controller 72 inserts the table 71 into the opening of the rotating body 32 in which the rotational center is included, and moves the table 71 out of the opening after completion of imaging. Additionally, the table controller 72 transmits positional control information such as moving amount of the table 71 and the current position of the table 71 to the scan controller 23.

The scan controller 23 includes, e.g., a non-illustrated processor such as a CPU and a memory. The scan controller 23 controls respective components of the gantry 21 such as the rotation controller 41, the high-voltage generator 61, the collimator controller 63, and the table controller 72 of the bed 22 in accordance with instructions inputted from the operation panel 24 and/or the console 12.

The operation panel 24 includes a display device such as a monitor in addition to an input device such as a touch panel and operation buttons, and is disposed at the side, front, or rear of the opening of the gantry 21. An operator inputs various types of instructions and imaging conditions from the operation panel 24 while confirming the state of the object Q. Specifically, the above instructions includes extinction and lighting of a non-illustrated projector configured to emit light for visually recognizing an X-ray irradiation range, movement, stop, and automatic feed of the table 71, and these instructions are inputted from the operation panel 24.

The console 12 of the X-ray CT apparatus 10 is configured on the basis of a computer, and can intercommunicate with an external device via a network such as a LAN (Local Area Network). The console 12 is configured of hardware such as processing circuitry 81, the above-described memory circuit 82, an input circuit 83, and a display 84. The processing circuitry 81 is interconnected with the respective hardware components constituting the console 12 via a bus as a transmission path of common signals. Incidentally, the console 12 is equipped with a memory-medium drive in some cases.

The processing circuitry 81 may be configured of a special-purpose hardware or be configured to implement various types of functions by software processing of its built-in processor. As an example here, a description will be given of a case where the processing circuitry 81 implements various types of functions by software processing of its processor.

The above-described term "processor" means, e.g., a circuit such as a special-purpose or general-purpose CPU, a special-purpose or general-purpose graphics processing unit (GPU), an application specific integrated circuit (ASIC), a programmable logic device, and a field programmable gate array (FPGA). The above-described programmable logic device includes, e.g., a simple programmable logic device (SPLD) and a complex programmable logic device (CPLD). The processing circuitry 81 implements various types of functions by reading out programs stored in the memory circuit 82 and executing the programs. Additionally or alternatively, the processing circuitry 81 implements various types of functions by reading out programs stored in its own processer and executing the programs.

Further, the processing circuitry 81 may be configured of a single processor or may be configured of a combination of plural processors which are independent of each other. In the latter case, plural memory circuits 82 may be provided for the respective processors so that programs executed by each processor are stored in the memory circuit 82 corresponding to this processor. As a further modification, one memory circuit 82 may collectively store all the programs corresponding to the respective functions of the plural processors.

The memory circuit 82 is configured of, e.g., a hard disc, an optical disc, and a semiconductor memory element such as a RAM (Random Access Memory) and a flash memory. The memory circuit 82 may be configured as a circuit to which a portable medium such as a USB (Universal Serial Bus) memory and a DVD (Digital Video Disk) is detachably connected. The memory circuit 82 stores image data and data necessary for executing programs in addition to various types of programs executed by the processing circuitry 81 (including an application program and an operating system). Additionally, the memory circuit 82 may store a program of a GUI (Graphical User Interface) which enables input of various types of commands for controlling the operating system from the input circuit 83.

The input circuit 83 is a circuit configured to output a signal which is inputted from an input device such as a pointing device. As an example here, the input device is assumed to be included in the input circuit 83. When the input device is operated by an operator, the input circuit 83 generates an input signal depending on this operation and outputs this input signal to the processing circuitry 81. The console 12 may be equipped with a touch panel which is equivalent to integration of the input device and the display 84.

The display 84 is a display device such as a liquid crystal display panel, a plasma display panel, and an organic EL (Electro Luminescence) panel. The display 84 displays an image under the control of the processing circuitry 81.

Projection data are inputted from the scanner 11 to the console 12. In the X-ray CT apparatus 10 of the first embodiment, projection data include high-resolution data and normal data. The console 12 stores projection data in the memory circuit 82, and generates a CT image by causing the processing circuitry 81 to reconstruct the projection data.

Figure 2:
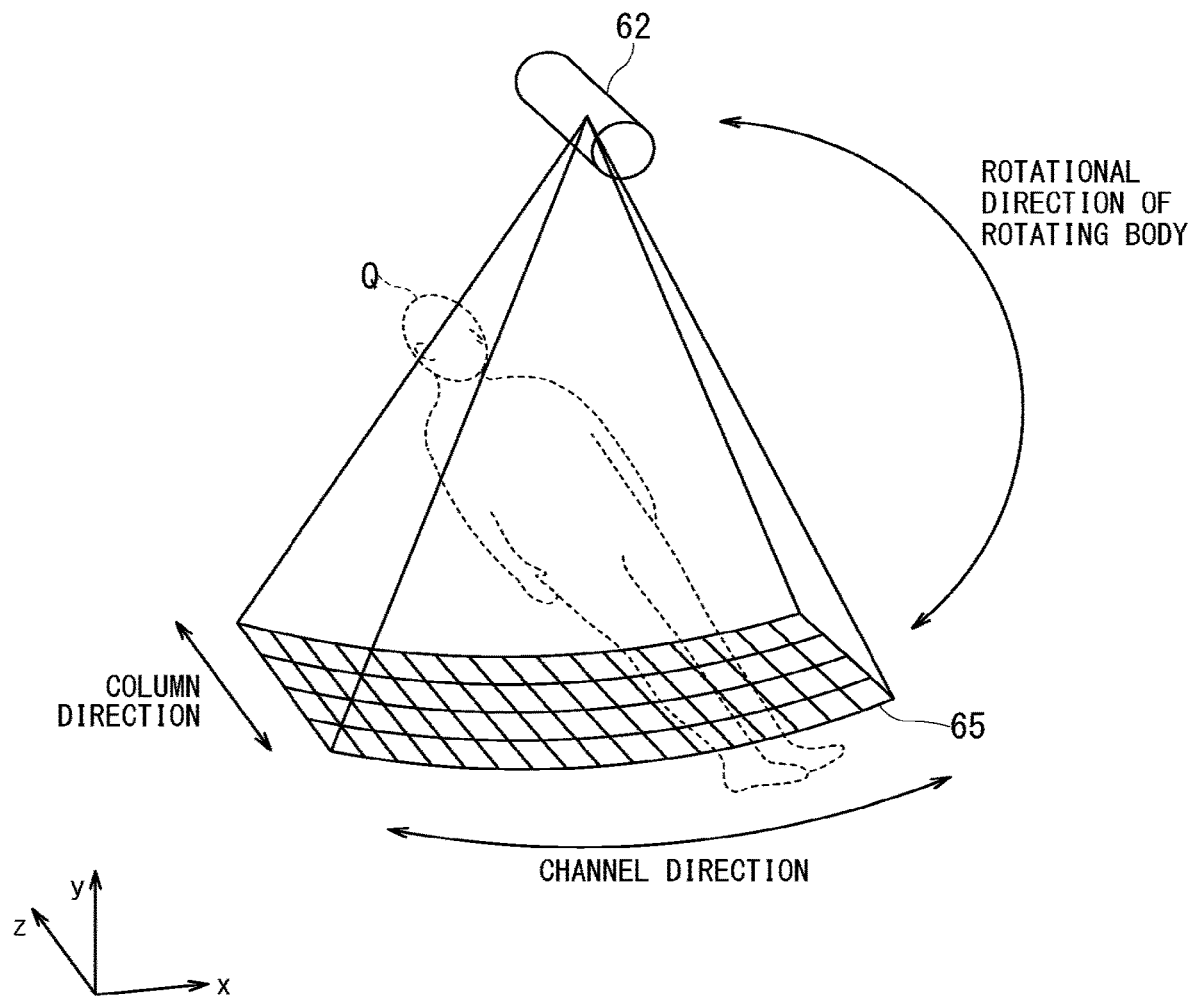
FIG. 2 is a schematic perspective view illustrating a two-dimensional array-type X-ray detector.

FIG. 2 is a schematic perspective view illustrating configuration of the X-ray detector 65 which is a two-dimensional array type. FIG. 2 shows the X-ray tube 62 which is an X-ray source, the object Q, and the X-ray detector 65. As an example in FIG. 2, the body axis direction of the object Q, i.e., the head-foot direction matches the Z-axis direction which is perpendicular to the Y-axis direction (i.e., vertical direction) in FIG. 1. In the X-ray detector 65, the direction in parallel with the body axis direction of the object Q is referred to as the column direction, and the direction perpendicular to the body axis direction of the object Q is referred to as the channel direction.

In FIG. 2, each of the plural lattices of the X-ray detector 65 indicates one detection element. In the two-dimensional array type X-ray detector 65, plural detection elements are arrayed in columns in the column direction and in rows in the channel direction.

Although FIG. 2 shows a case where the number of detection elements is 4 columns by 17 channels for simplicity, the number of detection elements is not limited to this case. In the actual X-ray detector 65, for instance, 64 or 320 detection elements are arrayed in the column direction and 256 or 512 detection elements are arrayed in the channel direction. Although FIG. 2 shows the case where detection elements are arrayed in a lattice pattern, arrangement of detection elements is not limited to the case of FIG. 2.

Figure 3:
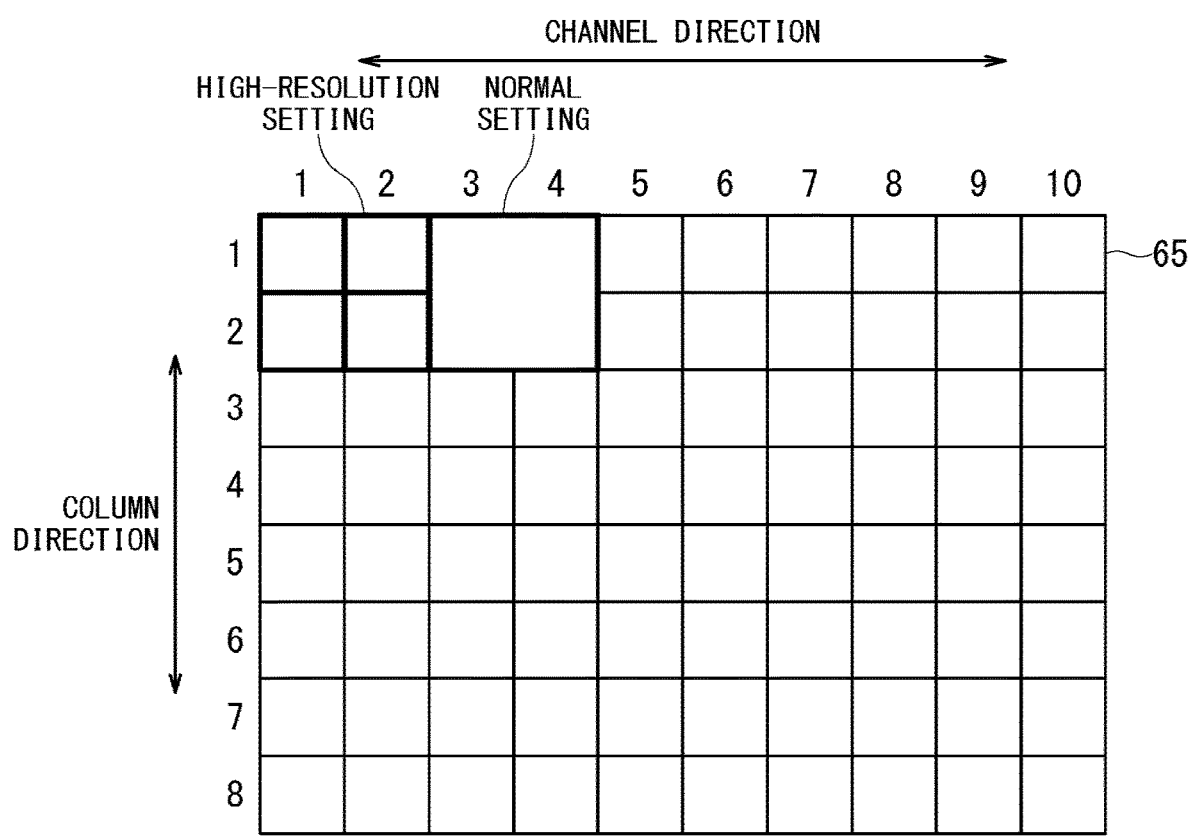
FIG. 3 is a schematic plan view illustrating a method of grouping detection elements.

FIG. 3 is a schematic plan view illustrating a method of grouping detection elements. FIG. 3 is schematic plan view when the X-ray detector 65 shown in FIG. 2 is viewed from the side of the X-ray tube 62. As an example here, the horizontal direction of the sheet of FIG. 3 is the channel direction of the X-ray detector 65, the longitudinal direction of the sheet of FIG. 3 is the column direction, and both directions are perpendicular to each other. For simplicity, FIG. 3 shows a case where a total of 80 detection elements are arrayed in 10 columns in the column direction and in 8 rows in the channel direction. In other words, each of the lattices shown in FIG. 3 corresponds to one detection element of the X-ray detector 65 except the one lattice which is larger in area than other lattices and is indicated as normal setting by a bold-line square.

Hereinafter, one set of grouped detection elements is referred to a detection-element group. Additionally, setting of detection-element groups for acquiring normal data is defined as normal setting, and setting of detection-element groups for acquiring high-resolution data is defined as high-resolution setting. In FIG. 3, the detection-element group of the high-resolution setting is indicated by four small lattices indicated by bold lines in the upper right part, and the detection-element group of the normal setting is indicated by a large lattice. As an example here, a description will be given of a case where each detection-element group is composed of four detection elements as shown by the bold-line frame indicative of the normal setting in the upper part of FIG. 3.

In FIG. 3, the number on the top side of all the detection elements and the number on the left side of all the detection elements indicate the position of each of the detection elements arrayed in the column direction and in the channel direction. In the following description, the position of each detection element is described as two numbers like coordinates such that the first number indicates the number in the channel direction and the second number indicates the number in the column direction. For instance, coordinates (1, 2) indicate the detection element which is in the first (i.e. topmost) row along the channel direction and is in the second column from the left along the column direction.

The above-described normal setting is to treat one set of detection elements as one detection element. In other words, in the normal setting, one detection-element group is regarded as one detection element. For instance, in FIG. 3, the four detection elements at (1, 3), (1, 4), (2, 3), and (2, 4) are grouped into one detection-element group, and is indicated by a large lattice. In the high-resolution setting, four X-ray signals outputted from the respective four detection elements at (1, 1), (1, 2), (2, 1), and (2, 2) are separately acquired as data of the respective X-ray signals of four pixels.

In FIG. 3, a description has been given of the X-ray detector 65 in which all the detection elements can acquire high-resolution data. However, the X-ray detector 65 is not limited to a detector which includes only the detection elements capable of acquiring high-resolution data. The X-ray detector 65 may include both types of detection elements, i.e., detection elements capable of acquiring high-resolution data and detection elements capable of acquiring normal data. For instance, the X-ray detector 65 may con- figured such that the central region of its arrangement plane of detection elements is composed of detection elements capable of acquiring high-resolution data and the rest region of its arrangement plane is composed of detection elements capable of acquiring normal data. The technique of the present invention can be applied to a region capable of acquiring high-resolution data in an X-ray detector which includes both types of detection elements (i.e., detection elements capable of acquiring high-resolution data and detection elements capable of acquiring normal data).

X-ray signals detected by the above-described detection elements are read out by plural DASs of the data acquisition circuit 66 under the control of the control circuitry 661. As to methods of reading out X-ray signals to be performed by the data acquisition circuit 66, there are a sequential readout mode and a simultaneous readout mode. In the sequential readout mode, one DAS reads out respective X-ray signals of plural detection elements in order. In the simultaneous readout mode, plural DASs simultaneously read out respective X-ray signals of plural detection elements. Hereinafter, the sequential readout mode will be described by referring to FIG. 4 to FIG. 6, and the simultaneous readout mode will be described by referring to FIG. 7 and FIG. 8.

Figure 4:
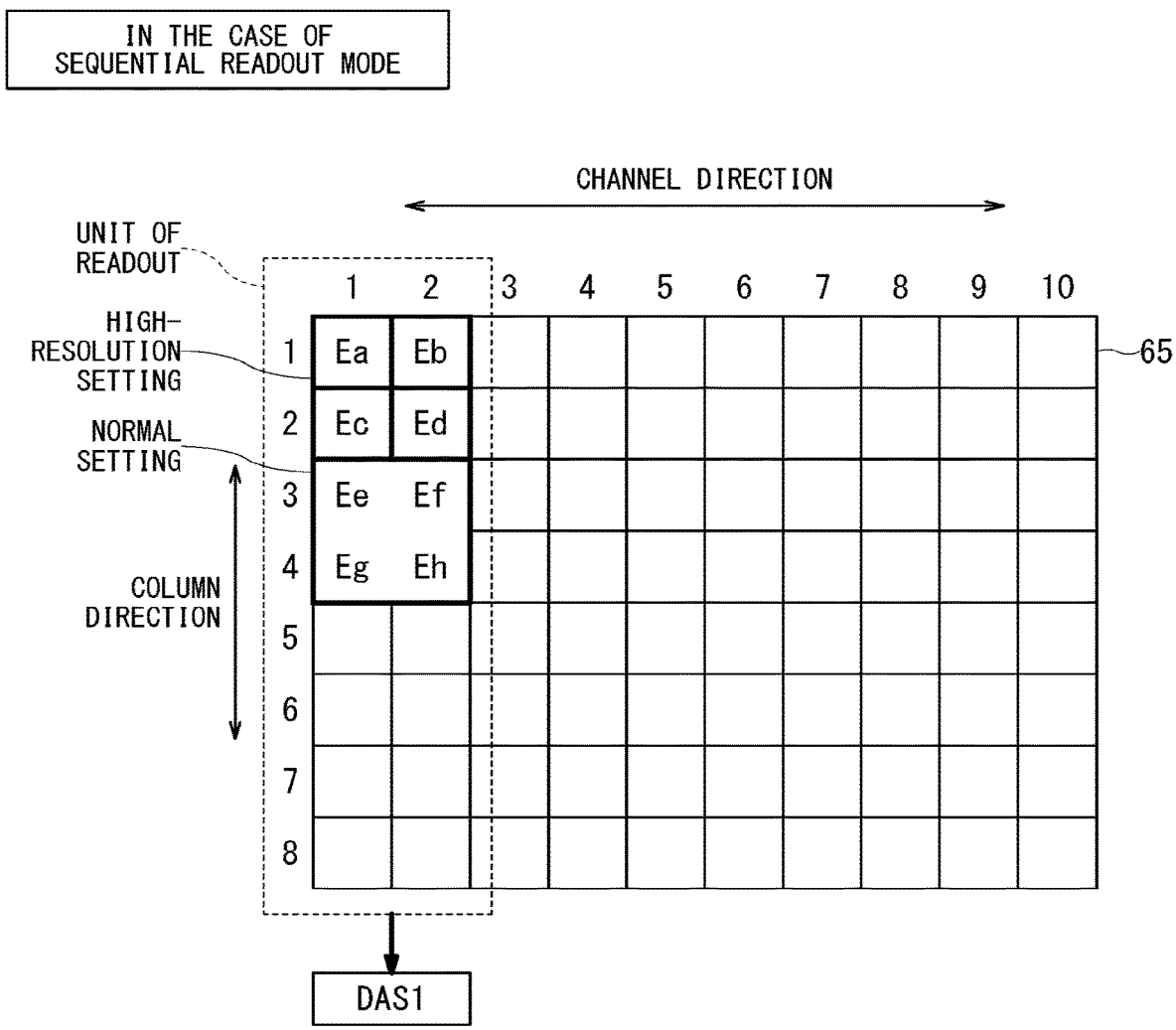
FIG. 4 is a schematic diagram illustrating a method of reading out X-ray signals in a sequential readout mode.

FIG. 4 is a schematic diagram illustrating a method of reading out X-ray signals in the sequential readout mode. In FIG. 4, a description will be given of a case where X-ray signals detected by respective detection elements of two columns along the column direction are read out by one DAS. In other words, as shown in FIG. 4, a description will be given of the case where the DAS 1 reads out respective X-ray signals of eight detection elements of the leftmost column starting the detection element at (1, 1) and respective X-ray signals of eight detection elements of the second leftmost column starting the detection element at (1, 2).

In the case of FIG. 4, the detection element Ea at (1, 1), the detection element Eb at (1, 2), the detection element Ec at (2, 1), and the detection element Ed at (2, 2) are set to the high-resolution setting, and the detection element Ee at (3, 1), the detection element Ef at (3, 2), the detection element Eg at (4, 1), and the detection element Eh (4, 2) are set to the normal setting.

Figure 5:
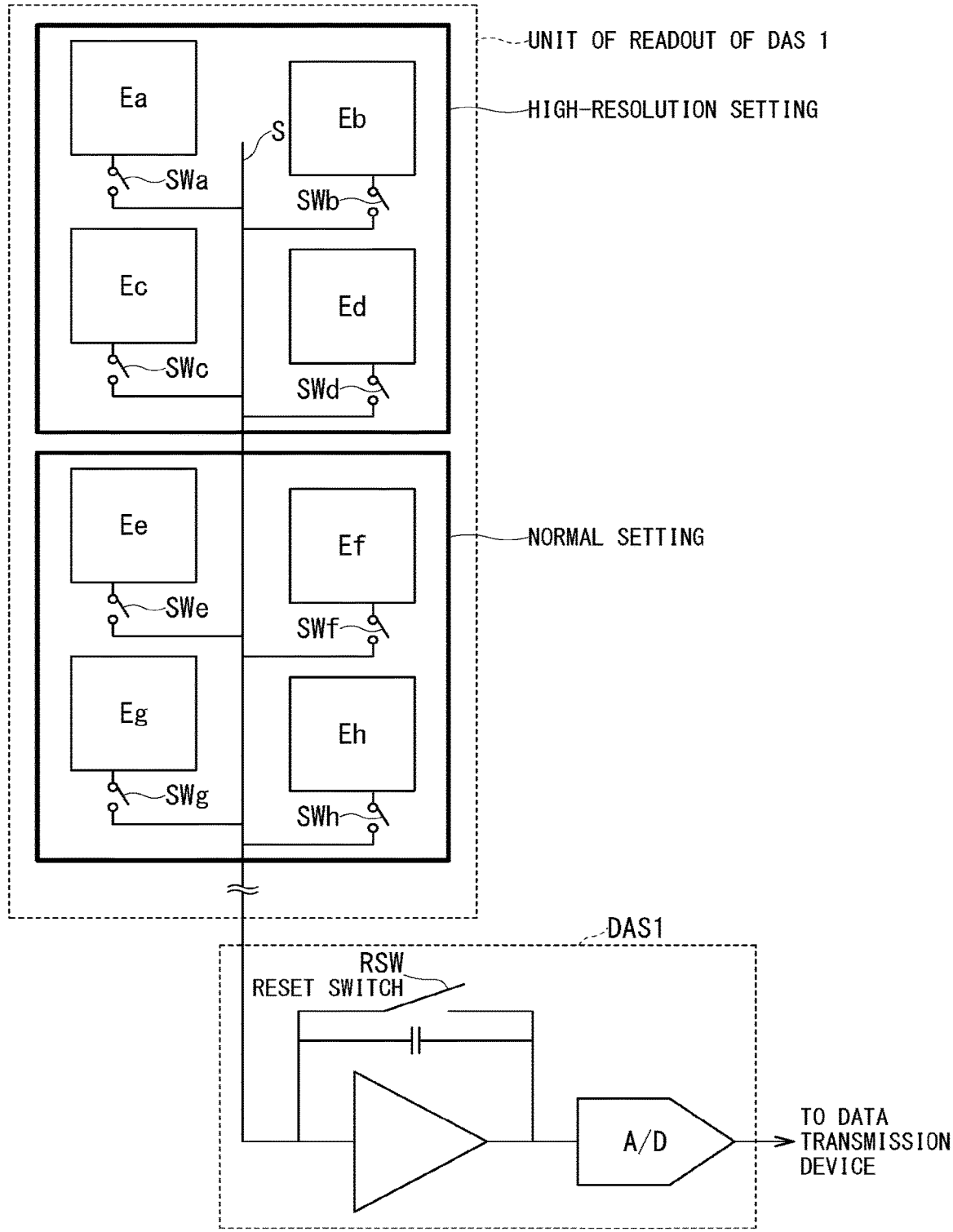
FIG. 5 is a schematic circuit diagram illustrating a method of reading out X-ray signals in the sequential readout mode.

FIG. 5 is a schematic circuit diagram illustrating a method of reading out X-ray signals in the sequential readout mode. FIG. 5 shows a schematic circuit diagram of the detection elements Ea, Eb, Ec, Ed, Ee, Ef, Eg, and Eh shown in FIG. 4. In FIG. 5, the group of the four detection elements Ea, Eb, Ec, Ed are set to the high-resolution setting, and the group of the four detection elements Ee, Ef, Eg, Eh are set to the normal setting in a manner similar to FIG. 4. The respective detection elements Ea, Eb, Ec, Ed, Ee, Ef, Eg, and Eh are connected to the DAS 1 via the output signal line S, and a switch is provided at the connection part between the output signal line S and each of detection elements Ea, Eb, Ec, Ed, Ee, Ef, Eg, and Eh. For instance, one end of the switch SWa is connected to the detection element Ea and the other end of the switch SWa is connected to the output signal line S. Similarly, the switch SWb is connected to the detection element Eb on its one end and is connected to the output signal line S on its other end.

In the sequential readout mode, the switches provided for the respective detection elements are switched in such a manner that X-ray signals of the respective detection elements are read out in order by the DAS 1. The DAS 1 is provided with a reset switch RSW, and can switch a detection element of a sampling target by switching the state of the reset switch RSW. In other words, the DAS 1 can separately read out X-ray signals of the respective detection elements by switching the reset switch RSW each time of reading out (i.e., sampling) an X-ray signal from one detection element. Conversely, the DAS 1 can consecutively read out X-ray signals of the respective detection elements of one detection-element group without switching the reset switch RSW so that those X-ray signals of one detection-element group are integrated and the integrated X-ray signal is read out as an X-ray signal of one detection-element group. In this manner, the DAS 1 separately reads out (i.e., samples) X-ray signals detected by respective detection elements which belong to a detection-element group of the high-resolution setting, and integrally reads out (i.e., samples) X-ray signals detected by respective detection elements which belong to a detection-element group of the normal setting. The switches of respective detection elements and the reset switch RSW of the DAS 1 are controlled by the control circuitry 661 via non-illustrated control signal lines connected to the control circuitry 661.

Figure 6:
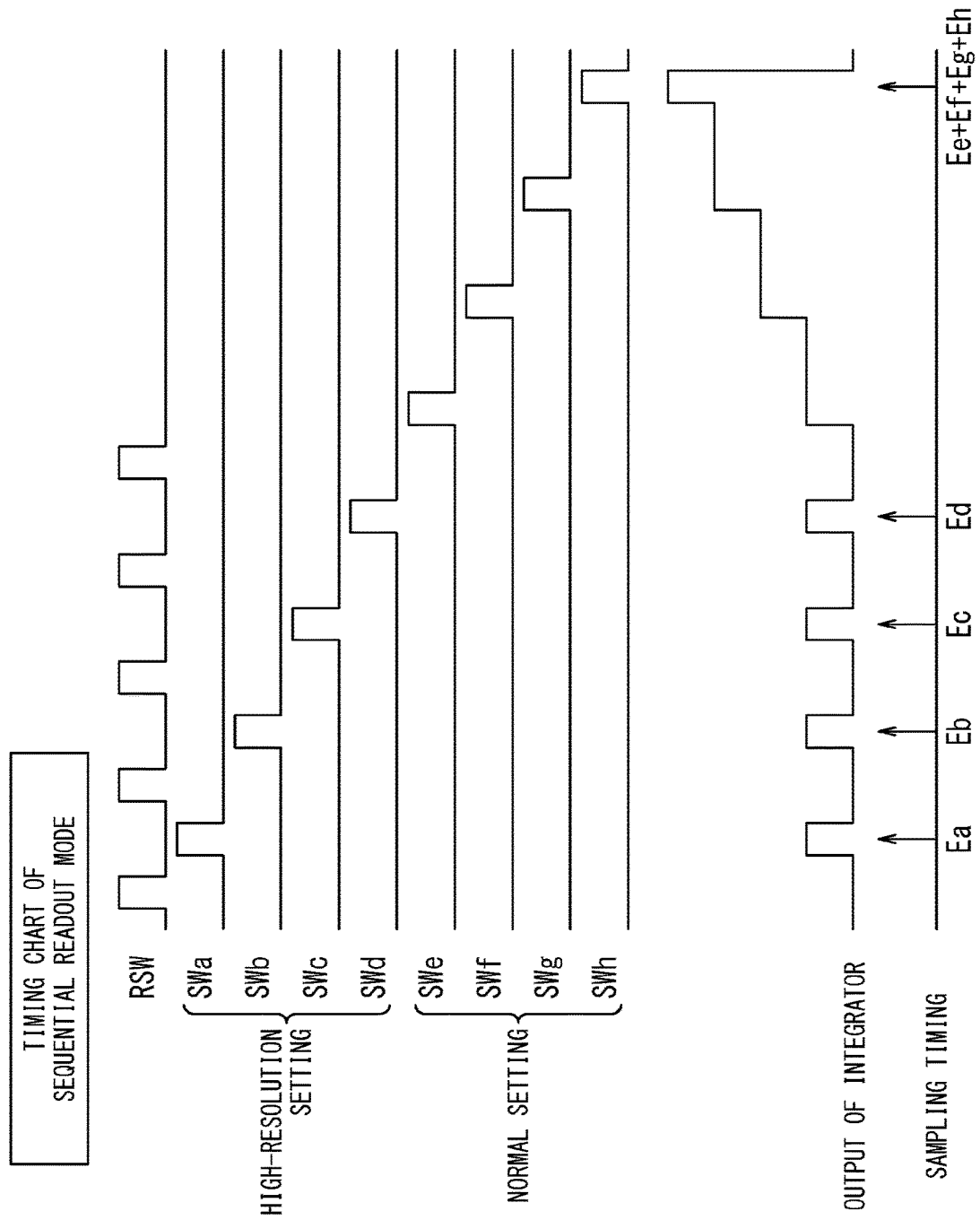
FIG. 6 is a timing chart illustrating an operation of reading out X-ray signals in the sequential readout mode.

FIG. 6 is a timing chart illustrating an operation of reading out X-ray signals in the sequential readout mode. FIG. 6 is a timing chart illustrating an operation of the circuit diagram shown in FIG. 5. FIG. 6 shows, from the top, respective timing charts for the reset switch RSW of the DAS 1, the switch SWa of the detection element Ea, the switch SWb of the detection element Eb, the switch SWc of the detection element Ec, the switch SWd of the detection element Ed, the switch SWe of the detection element Ee, the switch SWf of the detection element Ef, the switch SWg of the detection element Eg, and the switch SWh of the detection element Eh. Further, FIG. 6 shows a timing chart for output of an integrator of the DAS and a timing chart for timing of sampling an X-ray signal performed by the A/D converter.

In FIG. 6, a description will be given of the case where the detection-element group of the detection elements Ea, Eb, Ec, and Ed is set to the high-resolution setting and the detection-element group of the detection elements Ee, Ef, Eg, and Eh is set to the normal setting, in a manner similar to FIG. 5. As to the detection-element group of the high-resolution setting, the X-ray signals detected by the respective detection elements Ea, Eb, Ec, and Ed are separately read out (i.e., sampled) by the DAS 1. As to the detection-element group of the normal setting, the X-ray signals detected by the respective detection elements Ee, Ef, Eg, and Eh are integrally read out (i.e., sampled) by the DAS 1.

Specifically, when the switch SWa in FIG. 6 is brought into a closed state, i.e., on-state, the integrator of the DAS 1 reads out the X-ray signal of the detection element Ea, and the X-ray signal of the detection element Ea is sampled.

Next, the reset switch RSW is brought into the closed state such that electric charge of the integrator is emitted (i.e., reset). Afterward, under the state where the reset switch RSW is in the open state (i.e., off-state), the switch SWb is brought into the closed state (i.e., on-state) and thereby the X-ray signal of the detection element Eb is read out by the integrator.

Next, the reset switch RSW is brought into the closed state and the electric charge of the integrator is emitted. Afterward, under the state where reset switch RSW is in the off-state, the switch SWc is brought into the closed state and thereby the X-ray signal of the detection element Ec is read out by the integrator.

Next, the reset switch RSW is brought into the closed state and the electric charge of the integrator is emitted. Afterward, under the state where reset switch RSW is in the off-state, the switch SWd is brought into the closed state and thereby the X-ray signal of the detection element Ed is read out by the integrator. In this manner, the DAS 1 separately reads out the four X-ray signals of the respective detection elements Ea, Eb, Ec, and Ed of the detection-element group which is set to the high-resolution setting, in order.

Contrastively, when the X-ray signals are read out from the detection-element group of the normal setting, the integrator of the DAS 1 reads out the X-ray signal of the detection element Ee under the state where the reset switch RSW is open (i.e., in the off-state). Thus, under the state where the switch SWe is closed (i.e., in the on-state), the X-ray signal of the detection element Ee is read out by the integrator of the DAS 1.

Next, the switch SWf is brought into the closed state, and then the integrator reads out the X-ray signal of the detection element Ef in such a manner that the X-ray signal of the detection element Ee and the X-ray signal of the detection element Ef are summed up and accumulated as integrated electric charge.

Next, the switch SWg is brought into the closed state, then the integrator similarly reads out the X-ray signal of the detection element Eg, then the switch SWh is brought into the closed state, and then the integrator similarly reads out the X-ray signal of the detection element Eh.

In this manner, the integrator sequentially reads out the X-ray signals of the detection elements Ee, Ef, Eg, and Eh being set to the normal setting while the reset switch RSW is being kept in the off-state, in such a manner that the respective X-ray signals of the detection elements Ee, Ef, Eg, and Eh are summed up and accumulated. As described above, it is possible to integrate the respective X-ray signals of the four the detection elements Ee, Ef, Eg, and Eh by causing the integrator to sequentially read out those four X-ray signals while the reset switch RSW is being kept in the off-state.

The foregoing is the description of the sequential readout mode. Next, the simultaneous readout mode will be described. In the simultaneous readout mode, one DAS is provided for each detection element, and a DAS which reads out an X-ray signal is different depending on group setting.

Figure 7:
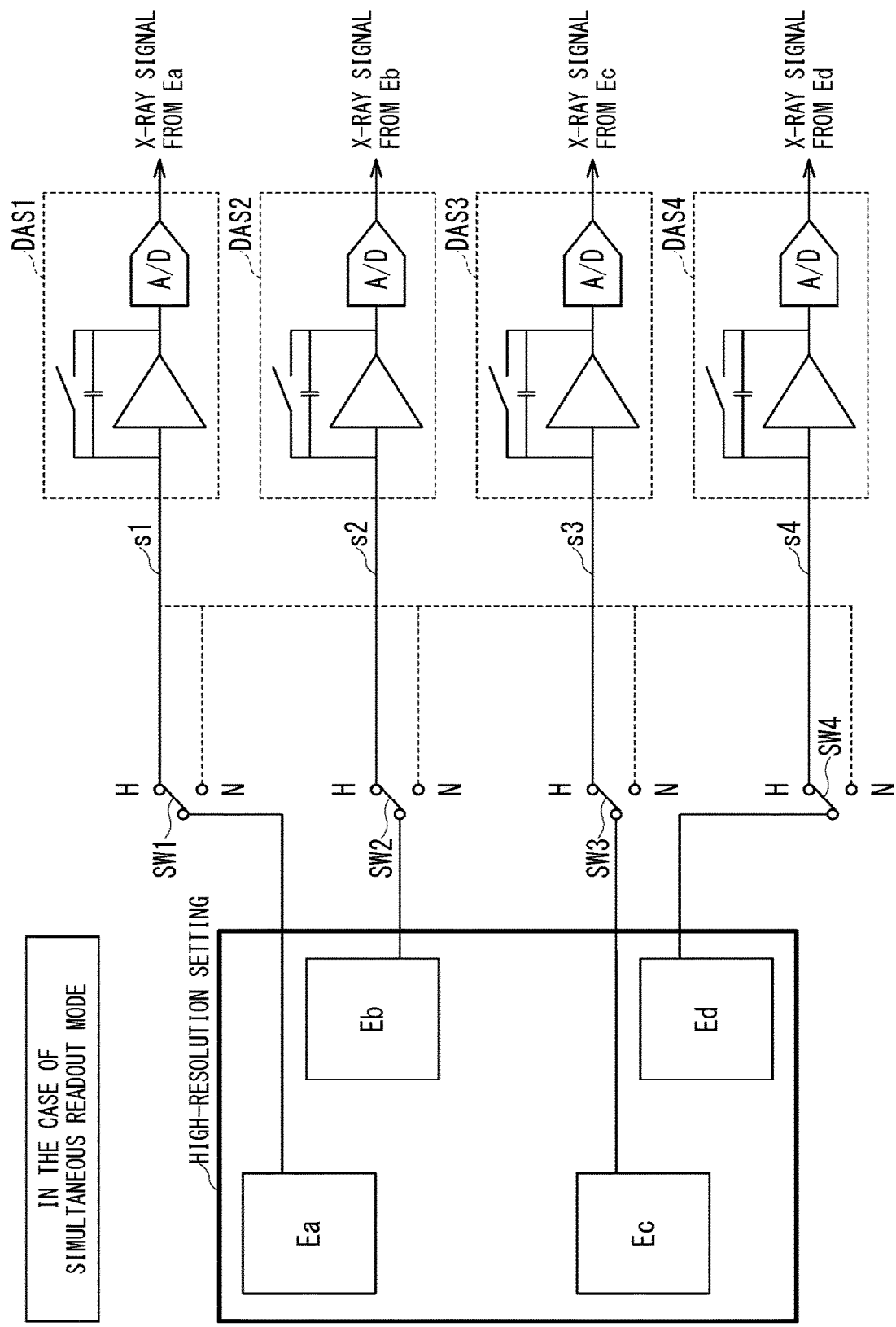
FIG. 7 is a schematic circuit diagram illustrating a method of reading out X-ray signals under high-resolution setting in the simultaneous readout mode.

FIG. 7 is a schematic circuit diagram illustrating a method of reading out X-ray signals from detection elements of the high-resolution setting in the simultaneous readout mode. The left side of FIG. 7 shows the detection-element group of the detection elements Ea, Eb, Ec, and Ed which are set to the high-resolution setting.

The detection element Ea is connected to the DAS 1 via the output signal line s1, and a three-way switch SW1 is provided at the connection part between the detection element Ea and the output signal line s1. This three-way switch SW1 can be connected to one of the contact point on the H-side and the contact point on the N-side. In the case of the high-resolution setting, the three-way switch SW1 is connected to the contact point on the H-side so that the DAS 1 reads out the X-ray signal of the detection element Ea via the output signal line s1.

Similarly, a three-way switch SW2 is provided between the detection element Eb and the DAS 2, and can be connected to one of the contact point on the H-side and the contact point on the N-side. In the case of the high-resolution setting, the three-way switch SW2 is connected to the contact point on the H-side so that the DAS 2 reads out the X-ray signal of the detection element Eb via the output signal line s2.

Similarly, a three-way switch SW3 is provided between the detection element Ec and the DAS 3, and can be connected to one of the contact point on the H-side and the contact point on the N-side. In the case of the high-resolution setting, the three-way switch SW3 is connected to the contact point on the H-side so that the DAS 3 reads out the X-ray signal of the detection element Ec via the output signal line s3.

Similarly, a three-way switch SW4 is provided between the detection element Ec and the DAS 4, and can be connected to one of the contact point on the H-side and the contact point on the N-side. In the case of the high-resolution setting, the three-way switch SW4 is connected to the contact point on the H-side so that the DAS 4 reads out the X-ray signal of the detection element Ed via the output signal line s4.

In the simultaneous readout mode, switching of the three-way switches SW1, SW2, SW3, and SW4 of the respective detection elements Ea, Eb, Ec, and Ed is simultaneously performed, and it is possible to simultaneously read out the respective X-ray signals from the four detection elements Ea, Eb, Ec, and Ed. As described in FIG. 7, when the detection-element group including the detection elements Ea, Eb, Ec, and Ed is set to the high-resolution setting, the X-ray signals detected by respective detection elements Ea, Eb, Ec, and Ed are separately read out by the DAS1, DAS2, DAS3, and DAS4 which respectively correspond to the detection elements Ea, Eb, Ec, and Ed. Contrastively, in the case of the normal setting, the X-ray signals of the detection elements Ea, Eb, Ec, Ed are integrally read out by one DAS.

Figure 8:
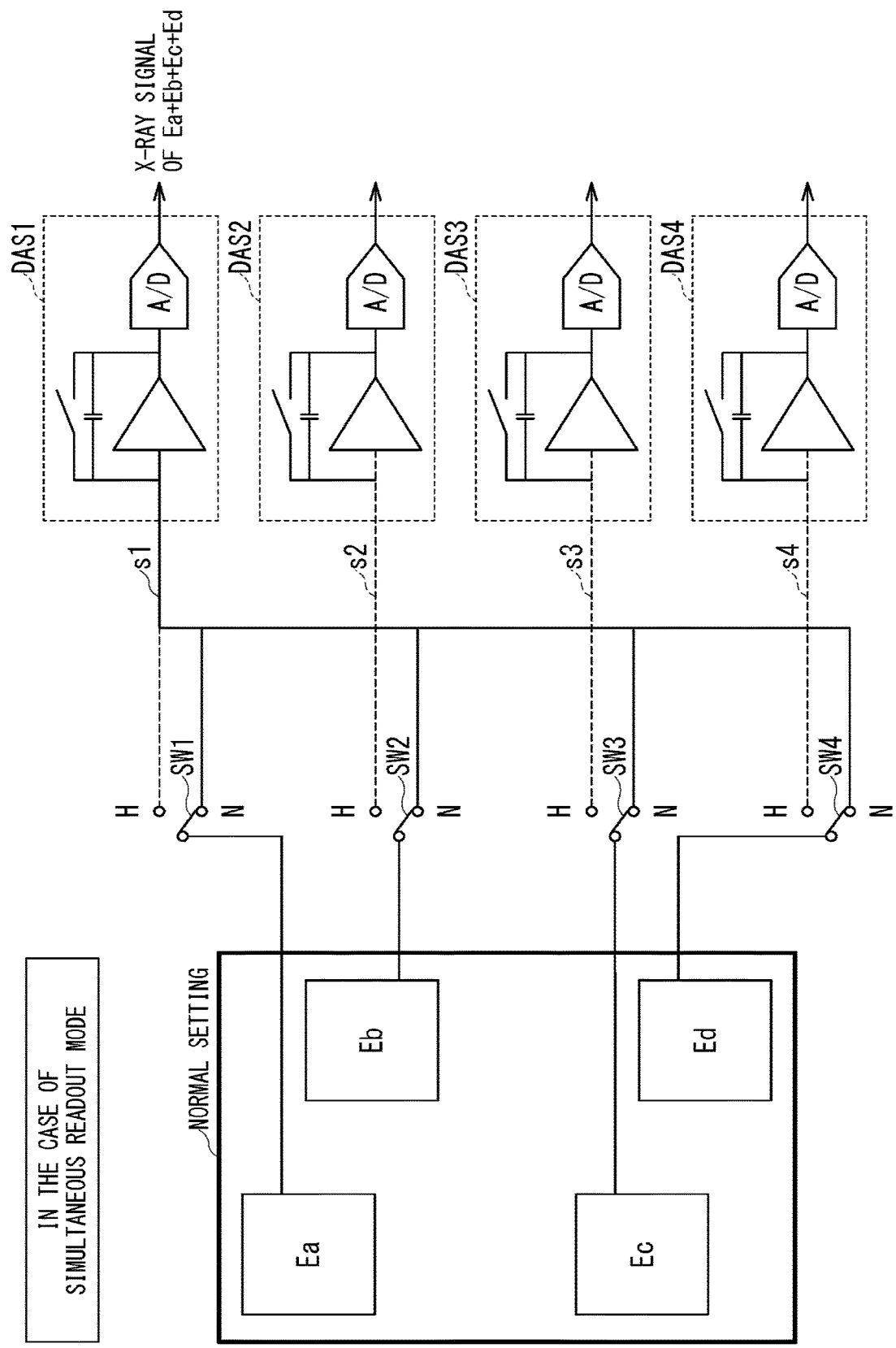
FIG. 8 is a schematic circuit diagram illustrating a method of reading out X-ray signals under normal setting in the simultaneous readout mode.

FIG. 8 is a schematic circuit diagram illustrating a method of reading out X-ray signals from detection elements of the normal setting in the simultaneous readout mode. FIG. 8 differs from FIG. 7 in that each of the three-way switches SW1, SW2, SW3, and SW4 respectively corresponding to the detection elements Ea, Eb, Ec, and Ed is connected to the contact point on the N-side and the four X-ray signals are integrally read out by the DAS 1 via the output signal line s1.

Specifically, the three-way switch SW1 is connected to the contact point on the N-side, and thereby the X-ray signal from the detection element Ea is read out by the DAS 1 via the output signal line s1. Similarly, the three-way switch SW2 is connected to the contact point on the N-side, and thereby the X-ray signal from the detection element Eb is read out by the DAS 1 via the output signal line s1. Similarly, the three-way switch SW3 is connected to the contact point on the N-side, and thereby the X-ray signal from the detection element Ec is readout by the DAS 1 via the output signal line s1. Similarly, the three-way switch SW4 is connected to the contact point on the N-side, and thereby the X-ray signal from the detection element Ed is read out by the DAS 1 via the output signal line s1. Since the X-ray signals of the respective detection elements Ea, Eb, Ec, and Ed are simultaneously (i.e., concurrently) read out by the DAS 1, the DAS 1 samples the summation of the four X-ray signals from the respective detection elements Ea, Eb, Ec, and Ed.

A description has been given of the methods of reading out X-ray signals to be performed by the data acquisition circuit 66 by referring to FIG. 4 to FIG. 8. The data acquisition circuit 66 is configured to read out X-ray signals under one of the sequential readout mode and the simultaneous readout mode. The data acquisition circuit 66 performs calibration processing for correction of zero-order offset and gain adjustment on the high-resolution data and the normal data being read out. A correction value for correcting zero-order offset differs between high-resolution data and normal data, and data for calibration differ between high-resolution data and normal data. Thus, the data acquisition circuit 66 may be configured to add mode flags for distinguishing between high-resolution data and normal data to respective data having been read out.

Figure 9:
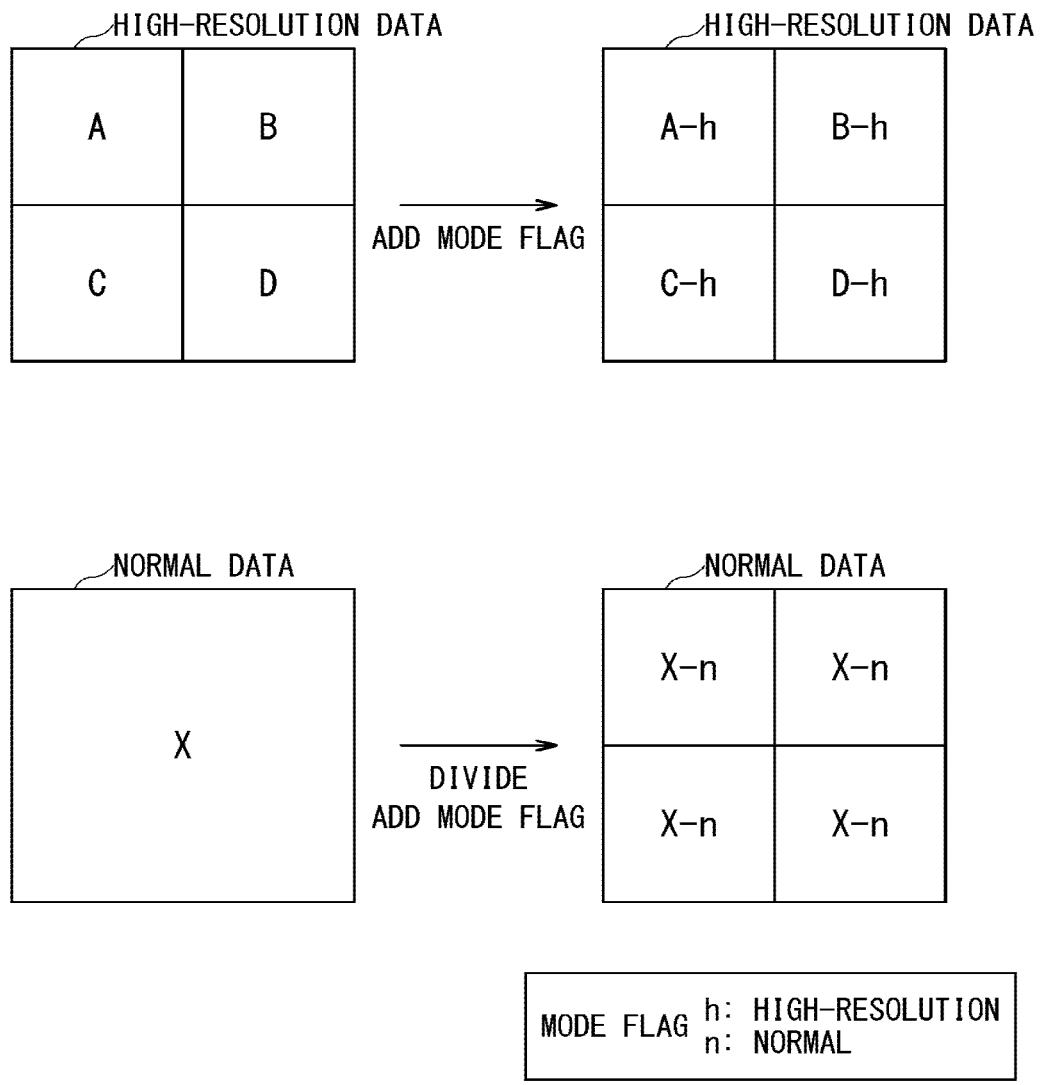
FIG. 9 is a schematic diagram illustrating a mode flag for distinguishing between high-resolution data and normal data.

FIG. 9 is a schematic diagram illustrating a mode flag for distinguishing between high-resolution data and normal data. The upper part of FIG. 9 shows high-resolution data, and the lower part of FIG. 9 shows normal data. FIG. 9 shows a case where "h" is added as a mode flag to each of high-resolution data and "n" is added as a mode flag to each of normal data, as shown in the lower right part.

The upper left part of FIG. 9 shows four original high-resolution data A, B, C, and D prior to addition of respective mode flags. After adding the mode flag "h" to each of the high-resolution data A, B, C, and D, the high-resolution data A, B, C, and D are respectively redefined as A-h, B-h, C-h, and D-h as shown in the upper right part of FIG. 9.

The lower left part of FIG. 9 shows one set of normal data X which is, e.g., integration of X-ray signals of four detection elements prior to addition of mode flags. The normal data X are divided into four which is the same data number as the high-resolution data A, B, C, and D, then a normal mode flag "n" is added to each of the four divided sections, and each of the four divided sections is redefined as "X-n" as shown in the lower right part of FIG. 9. Afterward, the normal data are outputted from the data acquisition circuit 66 to the data transmission device 52, and then stored in the memory circuit 82.

Thus, at the time of storing the normal data, the position in the channel direction and in the column direction of each of the original detection elements constituting those normal data does not shift but is correctly stored regardless of a scan mode. This effect holds true for the case of simultaneously storing normal data and high-resolution data.

The processing circuitry 81 determines a type of each data on the basis of mode flags added to respective high-resolution data and respective normal data, determines a correction value and data to be applied to correction and calibration depending on the determined data type, and performs the correction processing and the calibration processing.

In the normal setting as described above, data with a high S/N (Signal/Noise) ratio can be acquired by summing up respective X-ray signals detected by plural detection elements and treating the summation value as an X-ray signal from one detection element. Contrastively, in the high-resolution setting, since respective X-ray signals are acquired from plural detection elements, its S/N ratio is lower than the normal data but data with higher resolution can be obtained.

Although a description has been given of the case where four detection elements are treated as one detection-element group in FIG. 3 to FIG. 9 for avoiding complication, number of detection elements to be treated as one detection-element group is not limited to four. Number of detection elements to be treated as one detection-element group may be, e.g., two or eight. Additionally, though a description has been given of the case where each detection-element group consists of detection elements arranged in a lattice pattern in FIG. 3 to FIG. 8, an arrangement pattern of detection elements to be treated as one detection-element group is not limited to the above described cases.

Hereinafter, a description will be given of setting methods of detection elements performed by the X-ray CT apparatus 10 of the first embodiment with reference to FIG. 10 to FIG. 12. In each of FIG. 10 to FIG. 12, a description will be given of a case where the high-resolution setting is applied to some of a large number of detection elements and the normal setting is applied to the rest of those detection elements.

Figure 10:
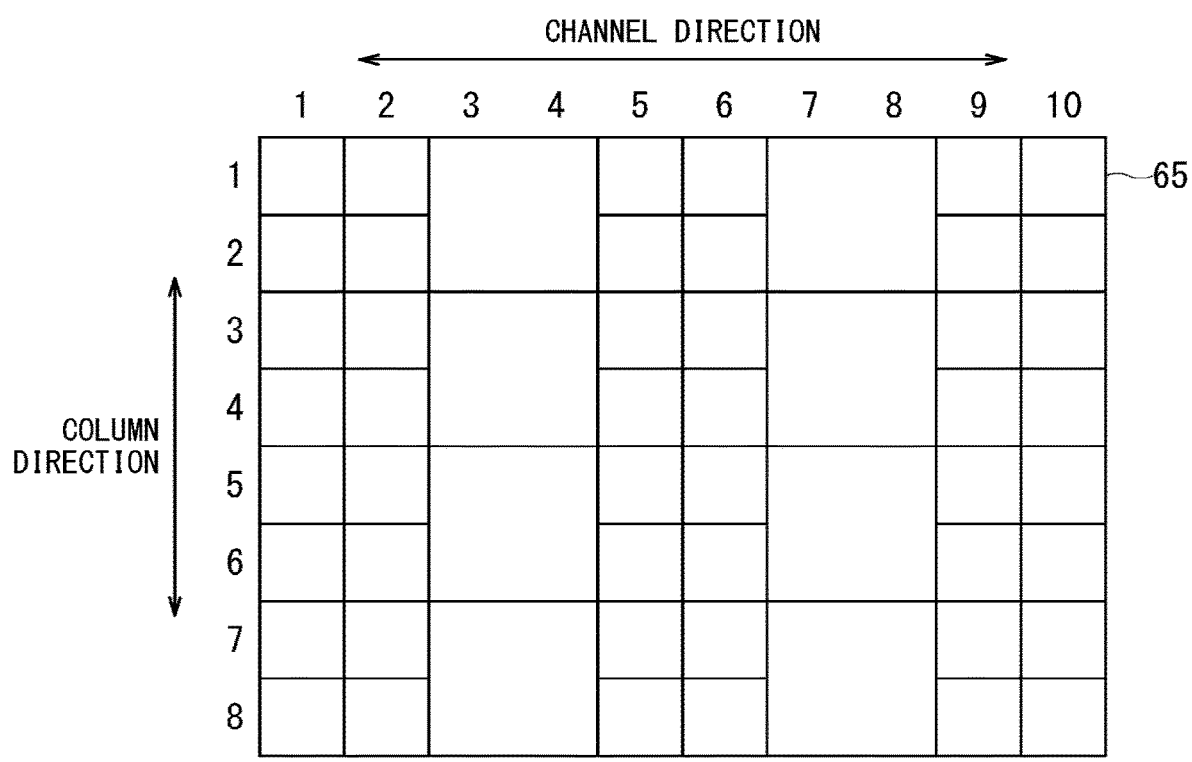
FIG. 10 is a schematic plan view illustrating the first setting case of detection elements in the first embodiment.

FIG. 10 is a schematic plan view illustrating the first setting case of detection elements in the first embodiment. As an example in FIG. 10, the channel direction is the horizontal direction of the sheet of FIG. 10 and the column direction is the longitudinal direction of the sheet of FIG. 10, in a manner similar to FIG. 3. Additionally, the position of each of the detection elements is indicated by the number on the top of the detection elements along the channel direction and the number on the left side of the detection elements along the column direction, in a manner similar to FIG. 3.

FIG. 10 shows a case where a setting method of detection-element groups is common to the column direction and is different in the channel direction. Further, FIG. 10 shows a case where each detection-element group being set to the normal setting is composed of four detection elements.

Each detection-element group being set to the normal setting is described as one frame which originally includes four detection elements arrayed in two columns in the column direction and in two rows in the channel direction, and each detection element which belongs to a detection-element group being set to the high-resolution setting is described as one lattice. This point holds true for FIG. 11 and FIG. 12.

The setting of detection-element groups in FIG. 10 shows a case where two columns of detection elements along the column direction being set to the high-resolution setting and two columns of detection elements along the column direction being set to the normal setting are alternately arranged in the channel direction.

As to arrangement of a column consisting of detection elements of the normal setting and a column consisting of detection elements of the high-resolution setting in the channel direction, it is not limited to the order shown in FIG. 10. For instance, a column consisting of detection elements of the normal setting may be arranged at predetermined intervals in the channel direction so that the rest is composed of columns consisting of detection elements of the high-resolution setting. Additionally or alternatively, a column consisting of detection elements of the normal setting may be arranged at random in the channel direction so that the rest is composed of columns consisting of detection elements of the high-resolution setting. Further, the ratio of the number of detection elements of the high-resolution setting to the number of detection elements of the normal setting is not limited to one to one, but may be determined depending on resolution and an S/N ratio of an image to be acquired.

Figure 11:
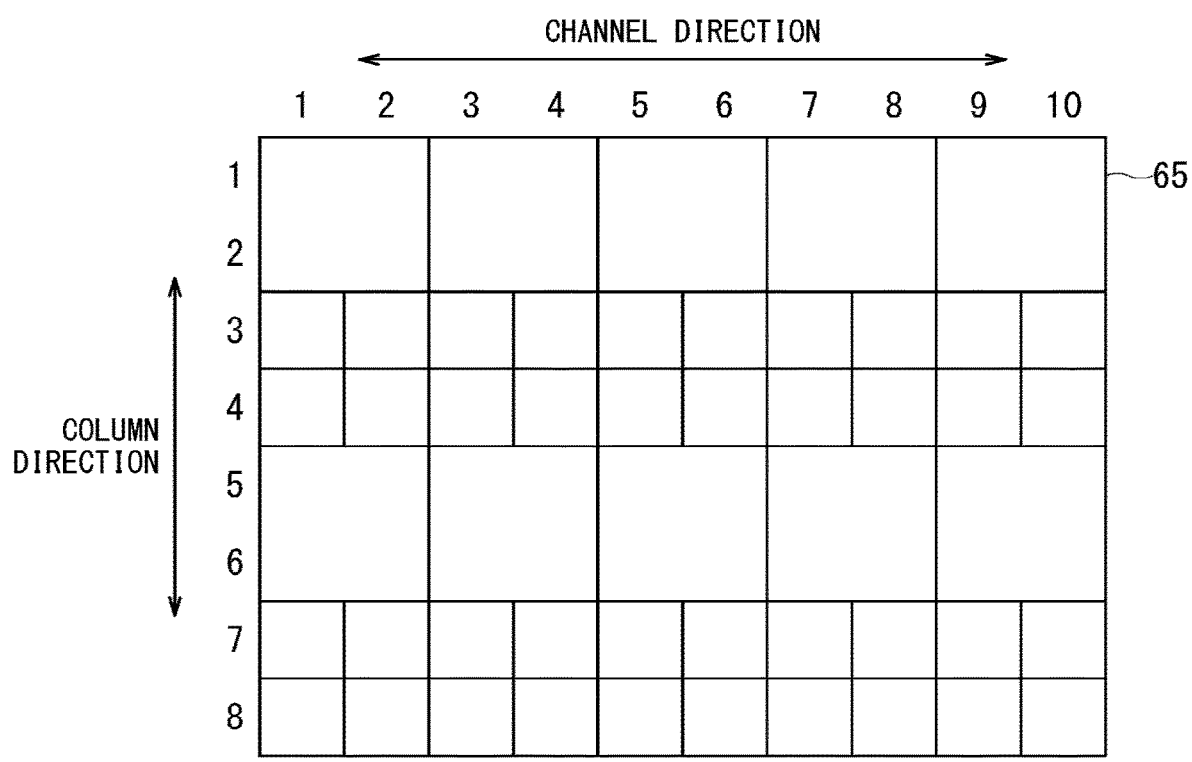
FIG. 11 is a schematic plan view illustrating the second setting case of detection elements in the first embodiment.

FIG. 11 is a schematic plan view illustrating the second setting case of detection elements in the first embodiment. FIG. 11 shows a case where a setting method of detection-element groups is common to the channel direction and is different in the column direction. Further, FIG. 11 shows a case where two rows of detection elements of the high-resolution setting along the channel direction and two rows of detection elements of the normal setting along the channel direction are alternately arranged in the column direction. As to arrangement of a row consisting of detection elements of the normal setting and a row consisting of detection elements of the high-resolution setting in the column direction, it is not limited to the order shown in FIG. 11, similarly to FIG. 10. For instance, a row consisting of detection elements of the normal setting may be arranged at predetermined intervals in the column direction so that the rest is composed of rows consisting of detection elements of the high-resolution setting. Additionally or alternatively, a row consisting of detection elements of the normal setting may be arranged at random in the column direction so that the rest is composed of rows consisting of detection elements of the high-resolution setting. Further, the ratio of the number of detection elements of the high-resolution setting to the number of detection elements of the normal setting is not limited to one to one, but may be determined depending on resolution and S/N ratio of an image to be acquired.

Figure 12:
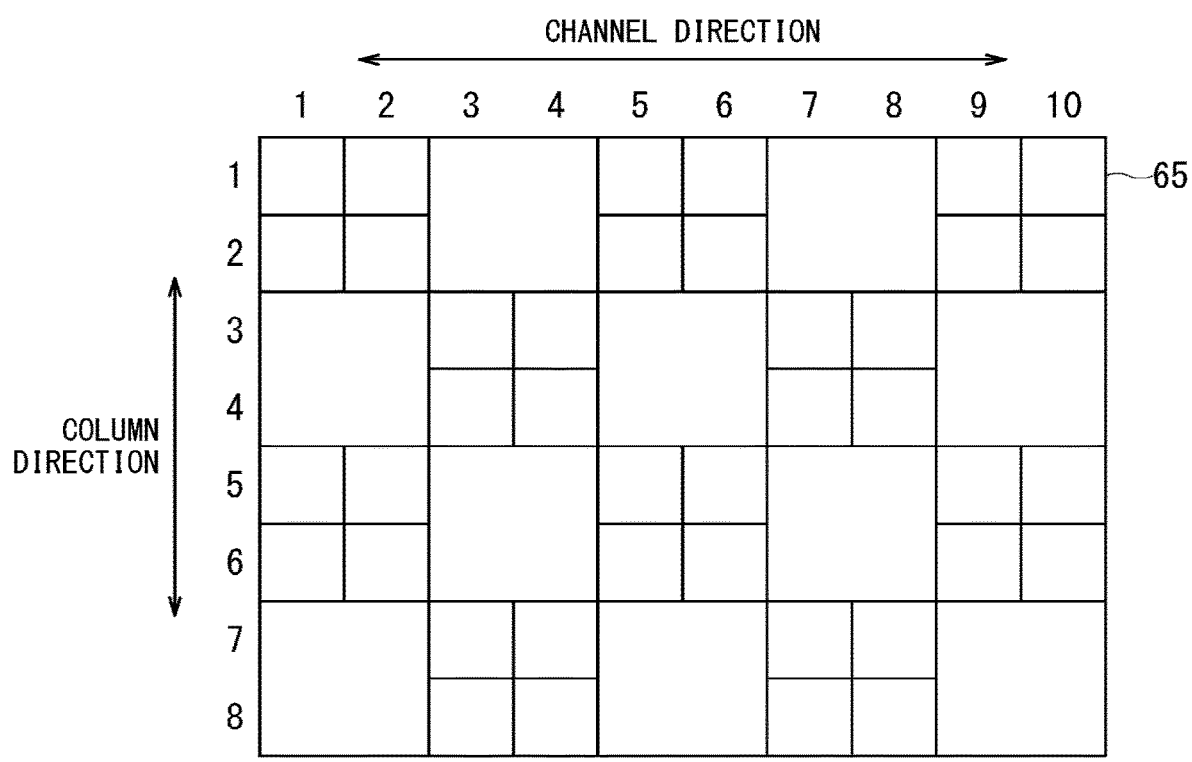
FIG. 12 is a schematic plan view illustrating the third setting case of detection elements in the first embodiment.

FIG. 12 is a schematic plan view illustrating the third setting case of detection elements in the first embodiment. In the case of FIG. 12, two types of detection-element groups are disposed in a staggered arrangement. One of the two types is set to the high-resolution setting and includes a total of four detection elements arranged in two rows and in two columns, and the other of the two types is set to the normal setting and includes a total of four detection elements arranged in two rows and in two columns. The detection-element groups of the high-resolution setting are not adjacent to each other but are in point contact with each other, and the same holds true for the detection-element groups of the normal setting. Thus, the same arrangement pattern is repeated every four rows along the channel direction and is repeated every four columns along the column direction.

Here, N is defined as a multiple of four. In the two adjacent columns including (N-3)th column and (N-2)th column along the column direction, the detection-element groups of the high-resolution setting and the detection-element groups of the normal setting are alternately arranged in the column direction such that the detection-element group of the high-resolution setting is disposed at the first and the second rows. Contrastively, in the two adjacent columns including (N-1)th column and Nth column along the column direction, the detection-element groups of the high-resolution setting and the detection-element groups of the normal setting are alternately arranged in the column direction such that the detection-element group of the normal setting is disposed at the first and the second rows.

As to a staggered arrangement of detection-element groups of the high-resolution setting and detection-element groups of the normal setting, it is not limited to the case of repeating the same pattern every four columns or four rows, similarly to the cases of FIG. 10 and FIG. 11. For instance, when each detection-element group of the normal setting is composed of a total of 9 detection elements arranged in three rows in the channel direction and in three columns in the column direction, detection-element groups of the high-resolution setting and detection-element groups of the normal setting can be disposed in a staggered arrangement by repeating the same pattern every six rows of detection elements along the channel direction.

The respective arrangement patterns described in FIG. 10, FIG. 11, and FIG. 12 can be used in combination. For instance, the arrangement pattern shown in FIG. 3 may be applied to a part of the arrangement region of all the detection elements of the X-ray detector 65, while the arrangement pattern shown in FIG. 10 or FIG. 11 is applied to another part of the arrangement region of all the detection elements.

As described above, it is possible to simultaneously acquire high-resolution data and normal data in one X-ray scan operation by applying the high-resolution setting to a part of the arrangement region of all the detection elements and applying the normal setting to the rest of the arrangement region of all the detection elements.

Next, a description will be given of a case where setting of detection elements is switched for each view by referring to FIG. 13 to FIG. 17. In the present specification, a view means one angular direction in a scan performed by the X-ray CT apparatus 10. First, a view will be described by referring to FIG. 13.

Figure 13:
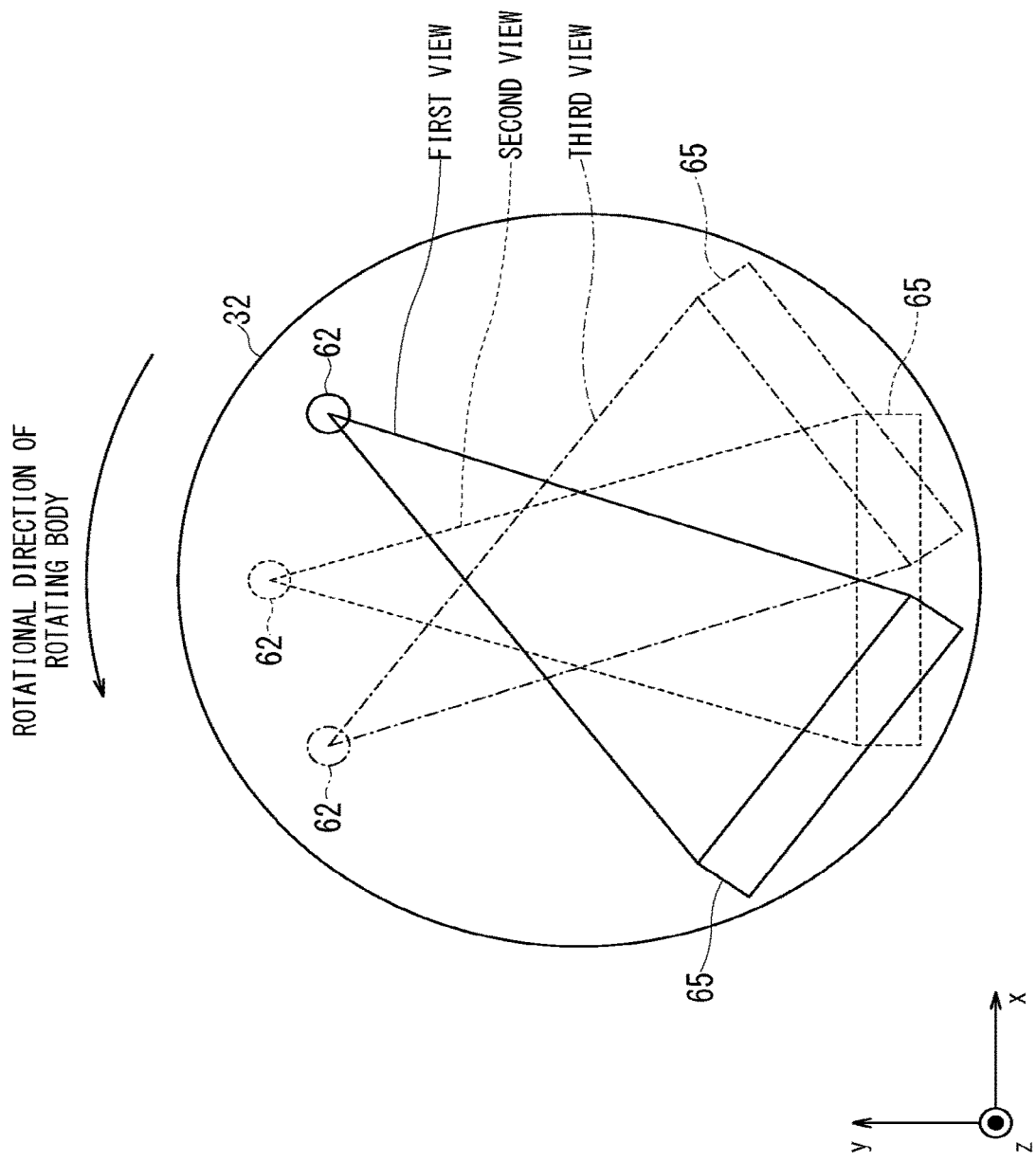
FIG. 13 is a schematic diagram illustrating definition of a view (i.e., one angular direction in a scan performed by an X-ray CT apparatus)

FIG. 13 is a schematic diagram illustrating definition of a view (i.e., one angular direction in a scan performed by an X-ray CT apparatus). As an example in FIG. 13, the X-ray tube 62 and the X-ray detector 65 of the rotating body 32 rotate counterclockwise in parallel with an X-Y plane of the apparatus coordinate system. A view is an imaging angle, and an imaging angle is determined by the position of the X-ray tube 62 and the X-ray detector 65 which rotate inside the rotating body 32.

As shown in FIG. 13, e.g., rotation of the rotating body 32 causes the X-ray tube 62 and the X-ray detector 65 to be sequentially positioned at the first view, then at the second view, and then at the third view such that respective projection data are acquired at the first to third views. In other words, the X-ray detector 65 detects X-rays radiated from the X-ray tube 62 at the first view indicated by solid lines such that the first projection data acquired. Next, the rotating body 32 further rotates and causes the X-ray tube 62 and the X-ray detector 65 to be positioned at the second view indicated by dashed lines, and the second projection data are acquired at the second view. Similarly, the rotating body 32 further rotates and the third projection data are acquired at the third view indicated by chain lines.

As described above, the X-ray CT apparatus 10 of the first embodiment performs each scan such that plural views are included in each scan. Additionally, one scan performed by the X-ray CT apparatus 10 of the first embodiment corresponds to imaging of acquiring one set of image data. For instance, one set of volume data are acquired by rotating the rotating body 32 by a half+α rotation, and this operation is also included in one scan. Further, it is also included in one scan to collectively acquire image data of the whole body of the object Q without stopping the rotation of the rotating body 32 and without changing radiation dose. As described above, one scan includes a case of causing the X-ray tube 62 to continuously radiate X-rays and a case of causing the rotating body 32 to continuously rotate.

Figure 14:
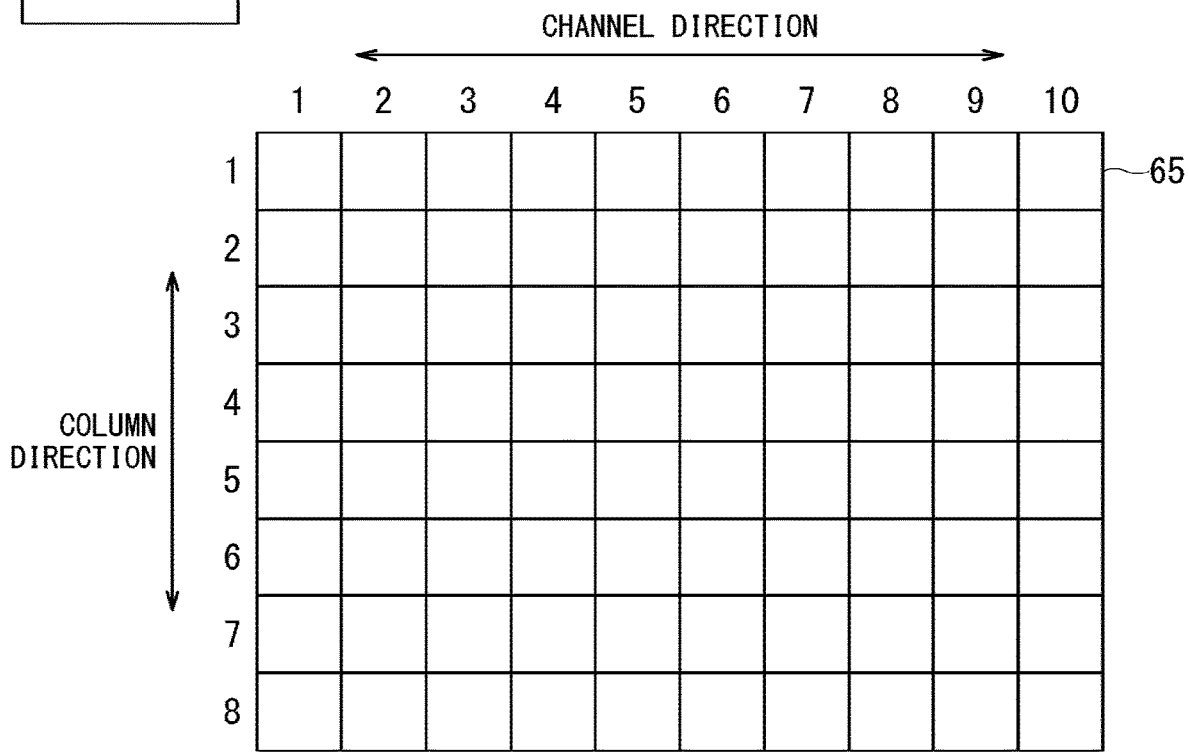
FIG. 14 is a schematic plan view illustrating the first case of switching setting of detection elements for each view in the first embodiment.
Figure 14:
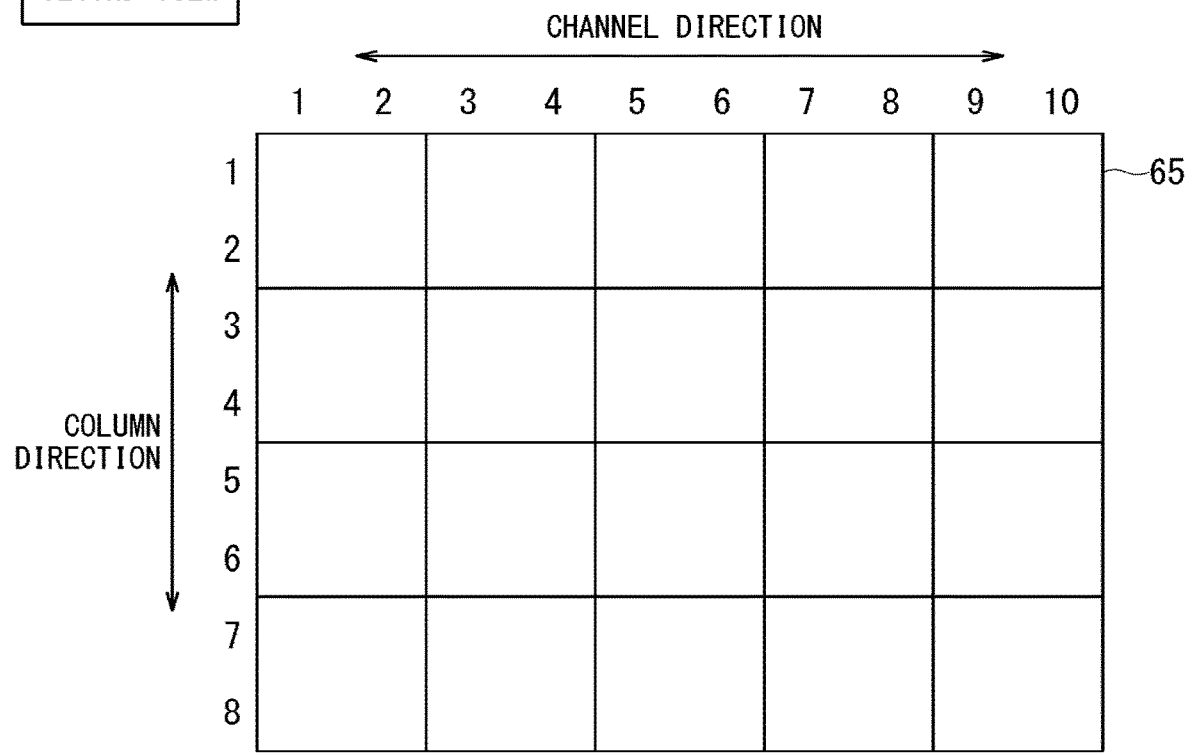

FIG. 14 is a schematic plan view illustrating the first case of switching setting of detection elements for each view in the first embodiment. The upper part of FIG. 14 shows setting of the X-ray detector 65 in the first view, and the lower part of FIG. 14 shows setting of the X-ray detector 65 in the second view. FIG. 14 shows a case where setting of detection elements is alternately switched for each view. Switching of the high-resolution setting and the normal setting may be performed at predetermined view intervals. Further, the ratio of frequency of using the high-resolution setting to frequency of using the normal setting is not limited to one to one.

It is possible to acquire both of high-resolution data and normal data in one scan by switching the setting of the X-ray detector 65 between the high-resolution setting and the normal setting for each view.

Figure 15:
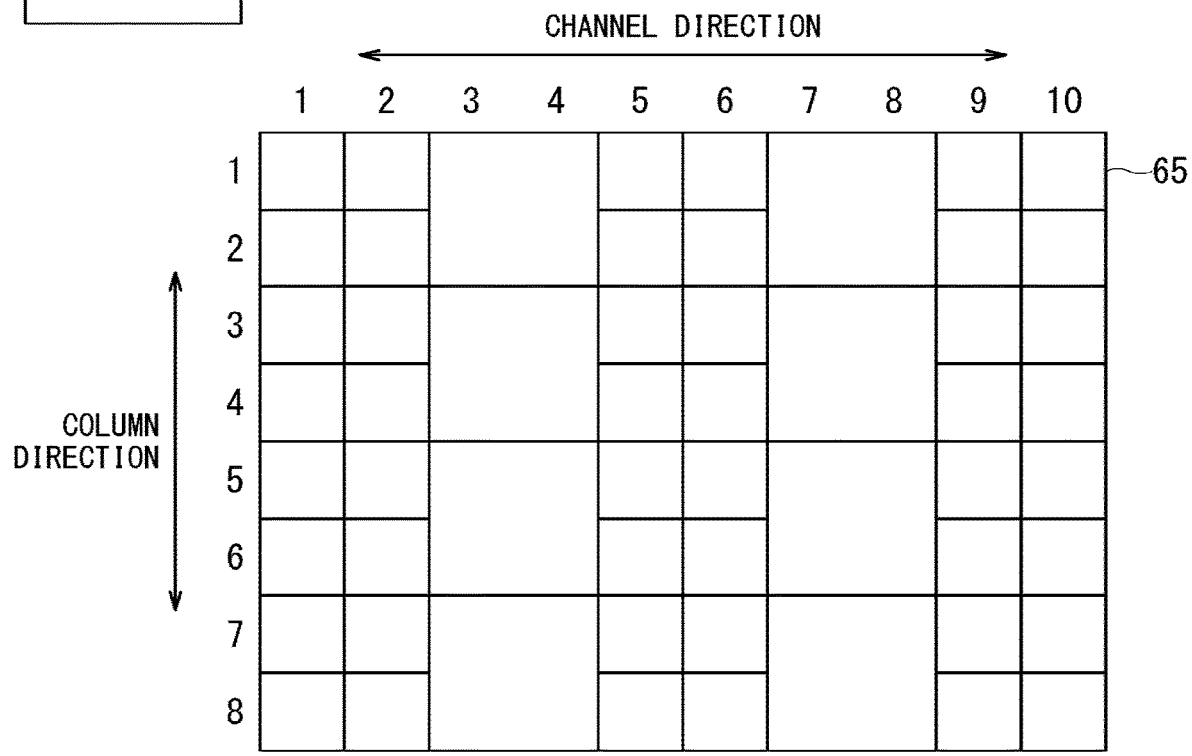
FIG. 15 is a schematic plan view illustrating the second case of switching setting of detection elements for each view in the first embodiment.
Figure 15:
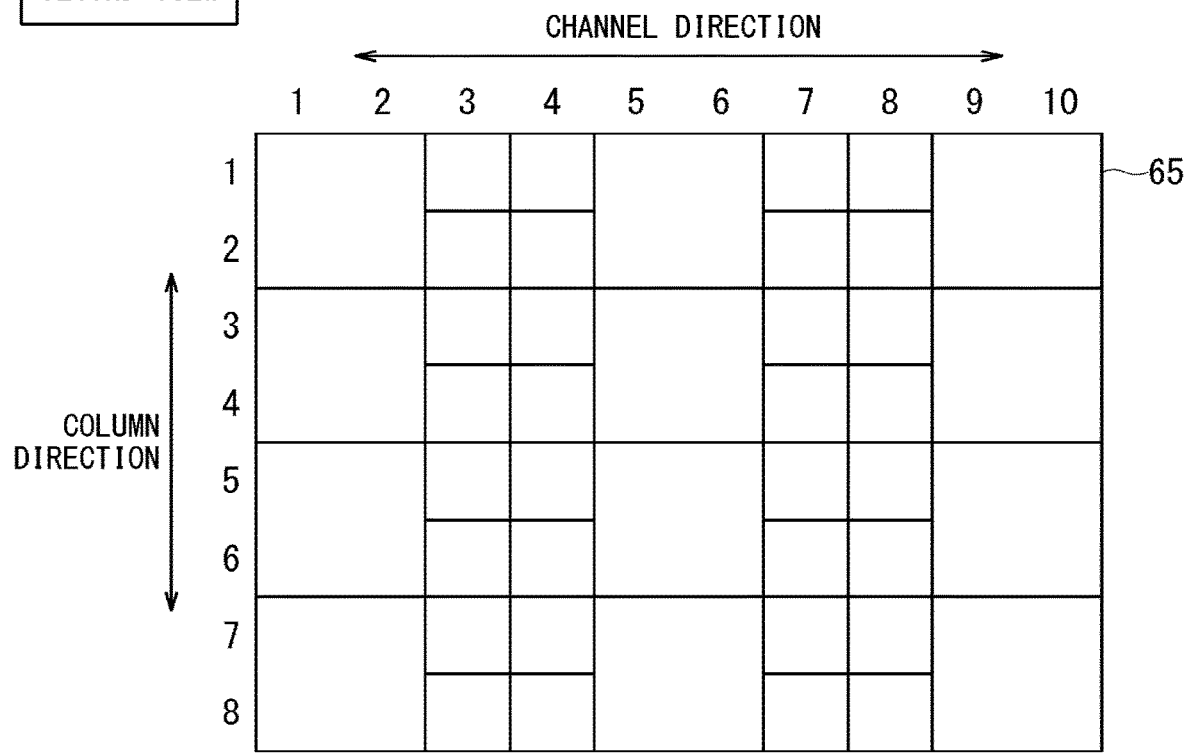

FIG. 15 is a schematic plan view illustrating the second case of switching setting of detection elements for each view in the first embodiment. The upper part of FIG. 15 shows the first view and the lower part of FIG. 15 shows the second view in a manner similar to FIG. 14.

The first view in FIG. 15 is set to the arrangement pattern of the high-resolution setting and the normal setting shown in FIG. 10. The second view in FIG. 15 is set to the arrangement pattern obtained by shifting the arrangement pattern shown in FIG. 10 by two columns in the channel direction (i.e., rightward on the sheet of FIG. 15). As to the arrangement pattern, shift amount in the channel direction may be one column. For instance, arrangement patterns of the respective views may be set in such a manner that each column of detection elements of the high-resolution setting and each column of detection elements of the normal setting in the first view are sequentially shifted by one column in the channel direction from the subsequent view.

As described above, FIG. 15 shows the case where the arrangement pattern is alternately switched between each odd-numbered view and each even-numbered view in a manner similar to FIG. 14.

Hereinafter, a description will be given of other cases where the arrangement pattern is alternately switched between each odd-numbered view and each even-numbered view, by referring to FIG. 16 and FIG. 17.

Figure 16:
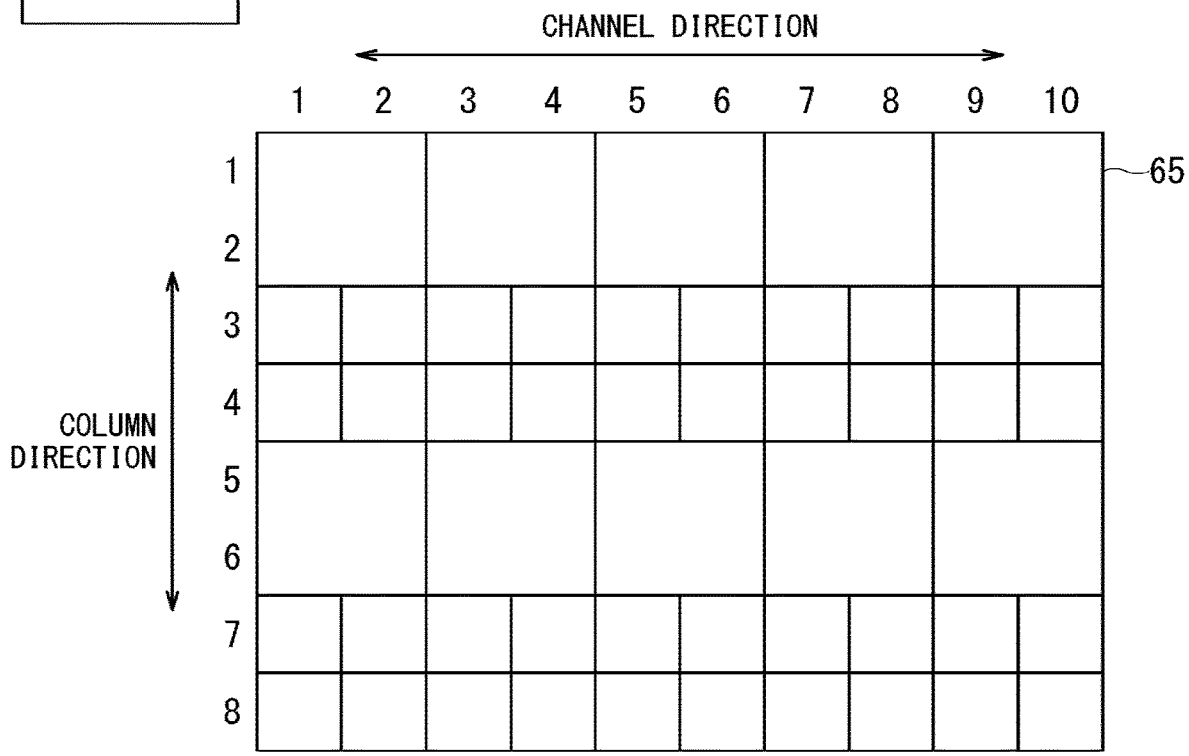
FIG. 16 is a schematic plan view illustrating the third case of switching setting of detection elements for each view in the first embodiment.
Figure 16:
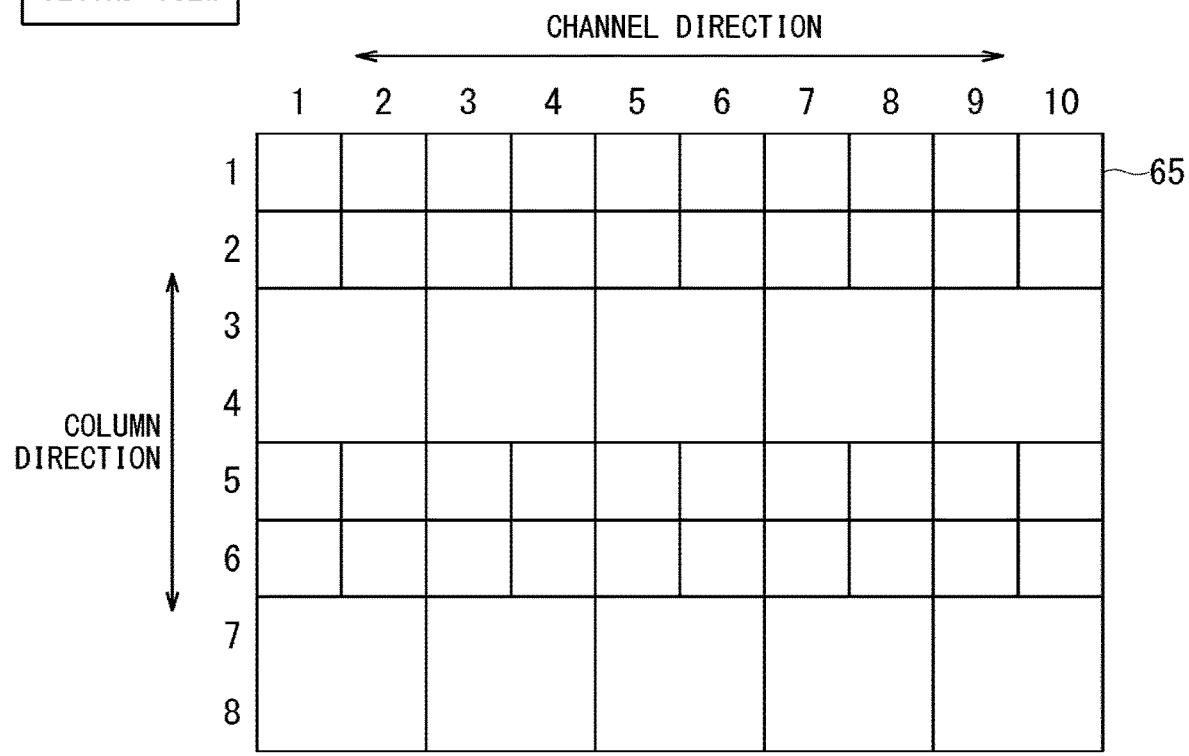

FIG. 16 is a schematic plan view illustrating the third case of switching setting of detection elements for each view in the first embodiment. The upper part of FIG. 16 shows the first view and the lower part of FIG. 16 shows the second view in a manner similar to FIG. 14.

The first view in FIG. 16 is set to the arrangement pattern of the high-resolution setting and the normal setting shown in FIG. 11. The second view in FIG. 16 is set to the arrangement pattern obtained by shifting the arrangement pattern shown in FIG. 11 by two rows in the column direction (i.e., upward on the sheet of FIG. 16). As to the arrangement pattern, shift amount in the column direction may be one row. For instance, arrangement patterns of the respective views may be set in such a manner that each row of detection elements of the high-resolution setting and each row of detection elements of the normal setting in the first view are sequentially shifted by one row in the column direction from the subsequent view.

Figure 17:
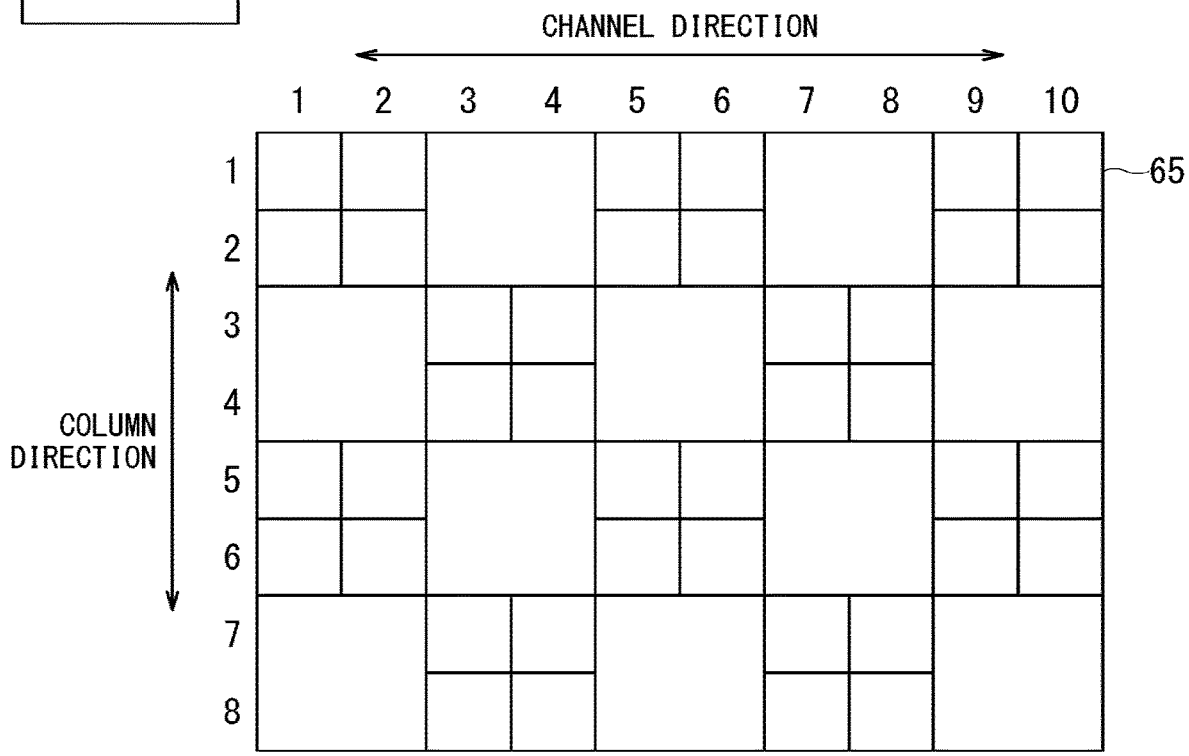
FIG. 17 is a schematic plan view illustrating the fourth case of switching setting of detection elements for each view in the first embodiment.
Figure 17:
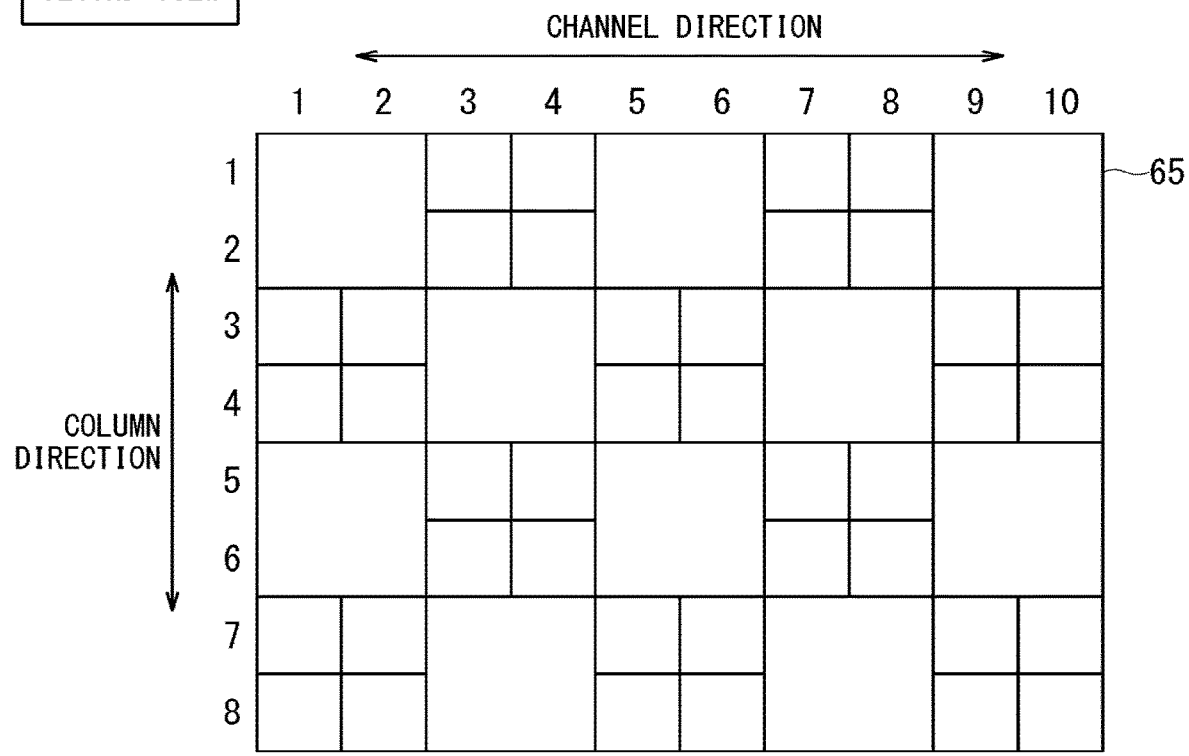

FIG. 17 is a schematic plan view illustrating the fourth case of switching setting of detection elements for each view in the first embodiment. The upper part of FIG. 17 shows the first view and the lower part of FIG. 17 shows the second view in a manner similar to FIG. 14.

The first view in FIG. 17 is set to the arrangement pattern of the high-resolution setting and the normal setting shown in FIG. 12. The second view in FIG. 17 is set to the arrangement pattern obtained by shifting the arrangement pattern shown in FIG. 12 by two rows in the column direction (or two columns in the channel direction). In other words, FIG. 17 shows a case where each even-numbered view is set to the arrangement pattern that is symmetric with respect to the arrangement pattern of each odd-numbered view.

Note that any two or more of the arrangement patterns shown in FIG. 15 to FIG. 17 can be used in combination. For instance, when NN is a multiple of three, it is possible to apply the arrangement pattern shown in the upper part of FIG. 15 to (NN-2)th view including the first view, apply the arrangement pattern shown in the upper part of FIG. 16 to (NN-1)th view including the second view, and apply the arrangement pattern shown in the upper part of FIG. 17 to NN-th view including the third view in order.

According to the X-ray CT apparatus 10 and the X-ray detection device 20 of the first embodiment as described above, both of high-resolution data and normal data can be acquired by one scan, and thus imaging time and X-ray dose can be reduced compared to conventional technology.

Additionally, when normal data are acquired by integrating high-resolution data after reading out those high-resolution data using the DASs, high-resolution data prior to the integration are subjected to A/D conversion by the DASs. For instance, when one set of normal data are acquired by integrating plural sets of high-resolution data through image processing, the plural sets of high-resolution data prior to the integration are separately subjected to A/D conversion by the respective DASs. Contrastively, when normal data are acquired under the normal setting, the X-ray signal integrated by the integrator is subjected to A/D conversion by each DAS. Since noise is in proportion to the number of times of A/D conversion, it is possible to acquire normal data with less noise under the normal setting, as compared with acquiring normal data by integrating high-resolution data through image processing or the like.

Since detection elements of the X-ray detector 65 can be switched between the high-resolution setting and the normal setting in the present embodiment, it is possible to acquire image data with less noise than the case of acquiring high-resolution data by using all the detection elements of an X-ray detector and then generating normal data from the acquired high-resolution data through image processing.

Second Embodiment

The second embodiment relates to a method of changing setting of detection elements described in the first embodiment depending on difference in X-ray signal intensity.

Figure 18:
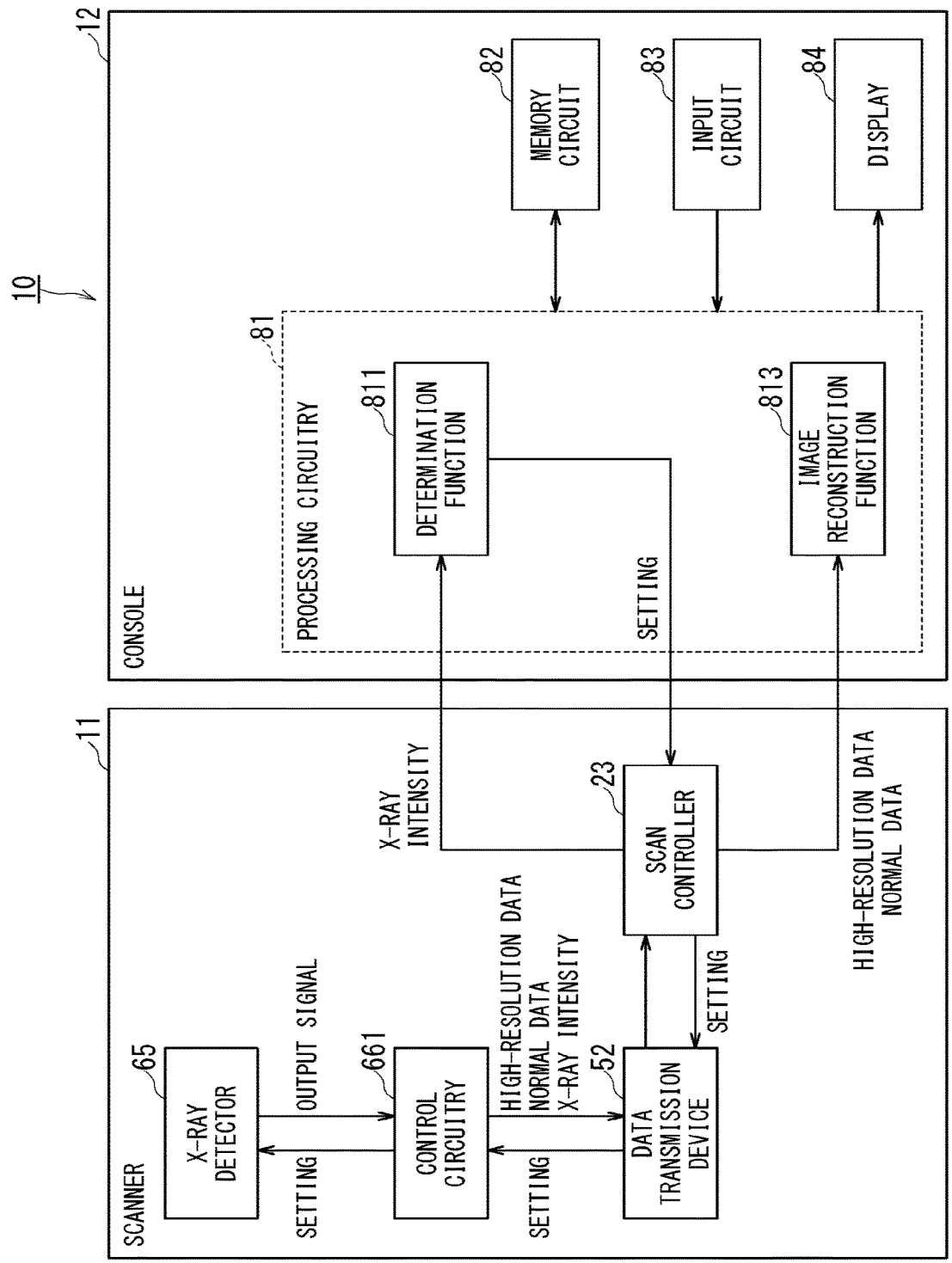
FIG. 18 is a functional block diagram illustrating configuration of the X-ray CT apparatus in the second embodiment.

FIG. 18 is a functional block diagram illustrating configuration of the X-ray CT apparatus 10 in the second embodiment. The processing circuitry 81 of the console 12 shown in FIG. 18 has a determination function 811 and an image reconstruction function 813. The determination function 811 and the image reconstruction function 813 are functions which the processor of the processing circuitry 81 implements by executing the corresponding programs stored in the memory circuit 82.

The determination function 811 determines setting of detection elements depending on X-ray signal intensity detected by the respective detection elements of the X-ray detector 65, and causes the control circuitry 661 to change setting of detection elements. For instance, when X-ray signal intensity detected under the high-resolution setting is low in the first view, there is a possibility that a predetermined S/N ratio cannot be maintained. In this case, an S/N ratio can be improved by changing setting of detection elements to the normal setting in the second view.

As described above, the determination function 811 determines whether setting of detection elements should be set to the high-resolution setting or the normal setting, on the basis of measured values of X-ray signal intensity detected by the respective detection elements.

The image reconstruction function 813 performs image reconstruction processing on the basis of projection data acquired by the scanner 11, and thereby an CT image is generated. The generated CT image is displayed on the display 84 and stored as image data in the memory circuit 82.

Figure 19:
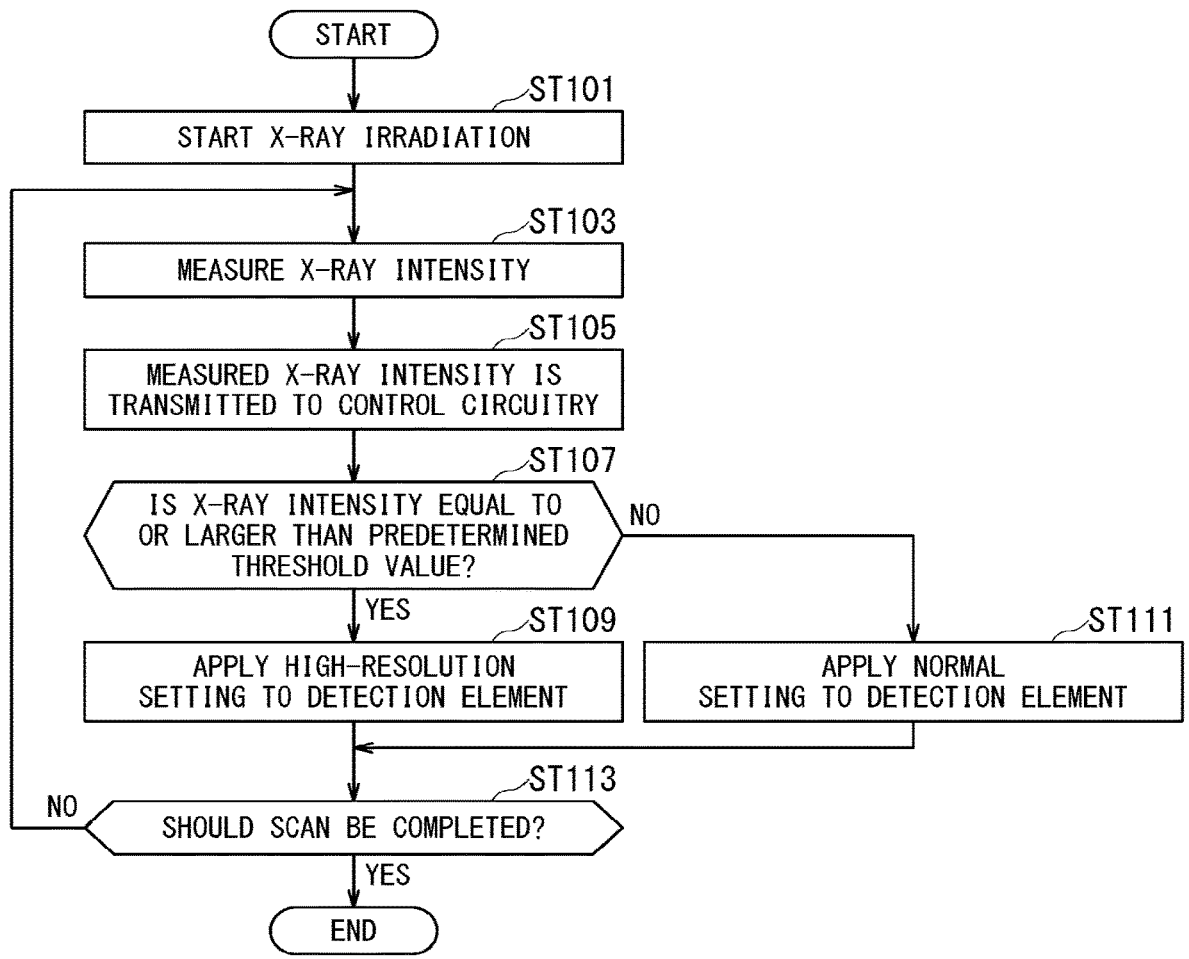
FIG. 19 is a flowchart illustrating an operation performed by the X-ray CT apparatus of the second embodiment.

FIG. 19 is a flowchart illustrating an operation performed by the X-ray CT apparatus 10 of the second embodiment. Hereinafter, the operation of the X-ray CT apparatus 10 in the second embodiment will be described according to the step number in the flowchart of FIG. 19.

In the step ST101, the X-ray tube 62 radiates X-rays toward the X-ray detector 65 in accordance with the tube voltage supplied from the high-voltage generator 61. In this manner, X-ray irradiation is started.

In the next step ST103, each of the detection elements of the X-ray detector 65 detects X-rays which have passed through the object Q in a certain view (e.g., the first view). On the basis of the detected X-rays, each of the detection elements measures X-ray signal intensity.

In the next step ST105, measured values of X-ray signal intensity are transmitted from the X-ray detector 65 (i.e., respective detection elements) to the control circuitry 661. Further, the data transmission device 52 transmits the measured values of X-ray signal intensity to the determination function 811 of the console 12 via the scan controller 23.

In the next step ST107, the determination function 811 determines whether a measured value of X-ray signal intensity is equal to or larger than a predetermined threshold value or not, for each detection element. On the basis of this determination result, the determination function 811 applies the high-resolution setting to each detection element which has measured X-ray signal intensity equal to or larger than the predetermined threshold value, and applies the normal setting to each detection element which has measured X-ray signal intensity smaller than the predetermined threshold value. This setting content determined by the determination function 811 is transmitted to the control circuitry 661 of the data acquisition circuit 66 via the scan controller 23. X-ray signal intensity of each detection-element group of the high-resolution setting may be determined on the basis of the average value of X-ray signal intensity measured by the respective detection elements of this group. Additionally, X-ray signal intensity of each detection-element group may be determined on the basis of the maximum value or the median value of X-ray signal intensity measured by the respective detection elements of this group. When it is determined that X-ray signal intensity of a certain detection-element group is equal to or larger than the predetermined threshold value, the processing proceeds to the step ST109 (corresponding to YES in the step ST107). Conversely, when it is determined that X-ray signal intensity of a certain detection-element group is smaller than the predetermined threshold value, the processing proceeds to the step ST111 (corresponding to NO in the step ST107).

In the step ST109, the control circuitry 661 applies the high-resolution setting to each detection-element group which is determined to have measured X-ray signal intensity equal to or larger than the predetermined threshold value.

In the step ST111, the control circuitry 661 applies the normal setting to each detection-element group which is determined to have measured X-ray signal intensity smaller than the predetermined threshold value. Incidentally, the setting for respective detection-element groups in the steps ST109 and ST111 is applied to each view subsequent to the view at which X-ray signal intensity is measured. For instance, setting of respective detection-element groups in the second view is changed on the basis of X-ray signal intensity measured in the first view.

In the next step ST113, the scan controller 23 determines whether a scan operation is completed or not. When a scan operation is continued, the processing returns to the step ST103 and the above-described operation is repeated. Conversely, when the scan controller 23 determines that a scan operation is completed, processing of completing the scan operation is performed (corresponding to YES in the step ST113).

Although application of one of the high-resolution setting and the normal setting to each detection-element group is determined and changed for each view in the above-described operation, embodiments of the present invention is not limited to such a case. For instance, application of the high-resolution setting or the normal setting to each detection-element group may be performed every predetermined number of views.

Additionally, the determination function 811 may determine which of the high-resolution setting and the normal setting is applied to each detection-element group, depending on change in X-ray signal intensity of each detection-element group for each view. X-ray signal intensity significantly changes at a border part of a structure. For instance, when the current view is moved from a body cavity region in the previous view to an organ region, change in X-ray signal intensity becomes large. In a body cavity region, X-ray permeability is high and X-ray signal intensity is high. Conversely, in a region where a structure such as an organ exists, X-ray permeability is lower and X-ray signal intensity is lower than a body cavity region. Thus, when the view is changed from a region with high X-ray signal intensity to another region with low X-ray signal intensity, it means that the view is changed from a body cavity region to, e.g., an organ region. It is desirable to acquire an high-resolution image or an image with a high S/N ratio for a view in which an organ exists. Thus, the determination function 811 may determine a border of a structure in a living body from difference in X-ray signal intensity so as to change setting of detection elements at the border. For instance, the determination function 811 may apply the high-resolution setting and the normal setting in such a manner that imaging is performed under the high-resolution setting for an organ region and imaging is performed under the normal setting for a region where high-resolution imaging is unnecessary like a body cavity.

Further, as to determining which of the high-resolution setting and the normal setting is applied to each detection element, the determination function 811 may use X-ray signal intensity measured at the time of imaging a scanogram image to be acquired prior to the main scan. A scanogram image is an image acquired by the X-ray CT apparatus 10 for selecting imaging conditions such as an imaging range, and is a two-dimensional image acquired by moving the X-ray tube 62 and the X-ray detector 65 in parallel with the body axis direction of the object Q.

The determination function 811 may measure X-ray signal intensity in the imaging range in advance on the basis of the scanogram image, and determine detection elements to be set to the high-resolution setting and detection elements to be set to the normal setting on the basis of the measured X-ray signal intensity prior to the main scan.

Additionally, the X-ray CT apparatus 10 may superimpose and display X-ray signal intensity on a scanogram image. This is so that the X-ray CT apparatus 10 may receive input for designating a range to be set to the high-resolution setting and a range to be set to the normal setting, from a user via the input circuit 83. In this case, the determination function 811 may determine which of the high-resolution setting and the normal setting is applied to respective detection elements, on the basis of the inputted range.

The arrangement patterns of the first embodiment described in FIG. 10 to FIG. 13 may be applied to the range of the X-ray detector 65 determined as the high-resolution setting by the determination function 811. In other words, not all the detection elements of the range determined as the high-resolution setting but some of the detection elements of this range may be set to the high-resolution setting by applying at least one of the arrangement patterns described in FIG. 10 to FIG. 13 to this range. Since it is possible to acquire both of high-resolution data and normal data in setting of detection elements described in the first embodiment, it is also possible to acquire high-resolution data from the range, where acquisition of high-resolution data is desired, by applying such setting of detection elements to this range in the second embodiment.

Additionally, by storing imaging conditions in the memory circuit 82, the determination function 811 can predict X-ray signal intensity on the basis of the stored imaging conditions such as dose of an X-ray beam, an irradiation range, shape of an X-ray beam, and radiation quality prior to start of a scan. The determination function 811 may determine which of the high-resolution setting and the normal setting is applied to respective detection-element groups, for each view on the basis of the predicted value of X-ray signal intensity.

According to the X-ray CT apparatus 10 of the second embodiment as described above, it is possible to dynamically switch between the high-resolution setting and the normal setting, one of which is applied to each detection-element group, depending on X-ray signal intensity. Thus, on the basis of X-ray signal intensity measured in a certain view of one scan, it is possible to dynamically change which of the high-resolution setting and the normal setting is applied to each detection-element group in the subsequent view. Additionally, by dynamically switching the setting of detection elements as described above, it is possible to acquire image data while resolution and an S/N ratio are being adjusted to become optimum.

Third Embodiment

The third embodiment relates to a method of changing setting of detection element described in the first embodiment depending on imaging conditions.

Figure 20:
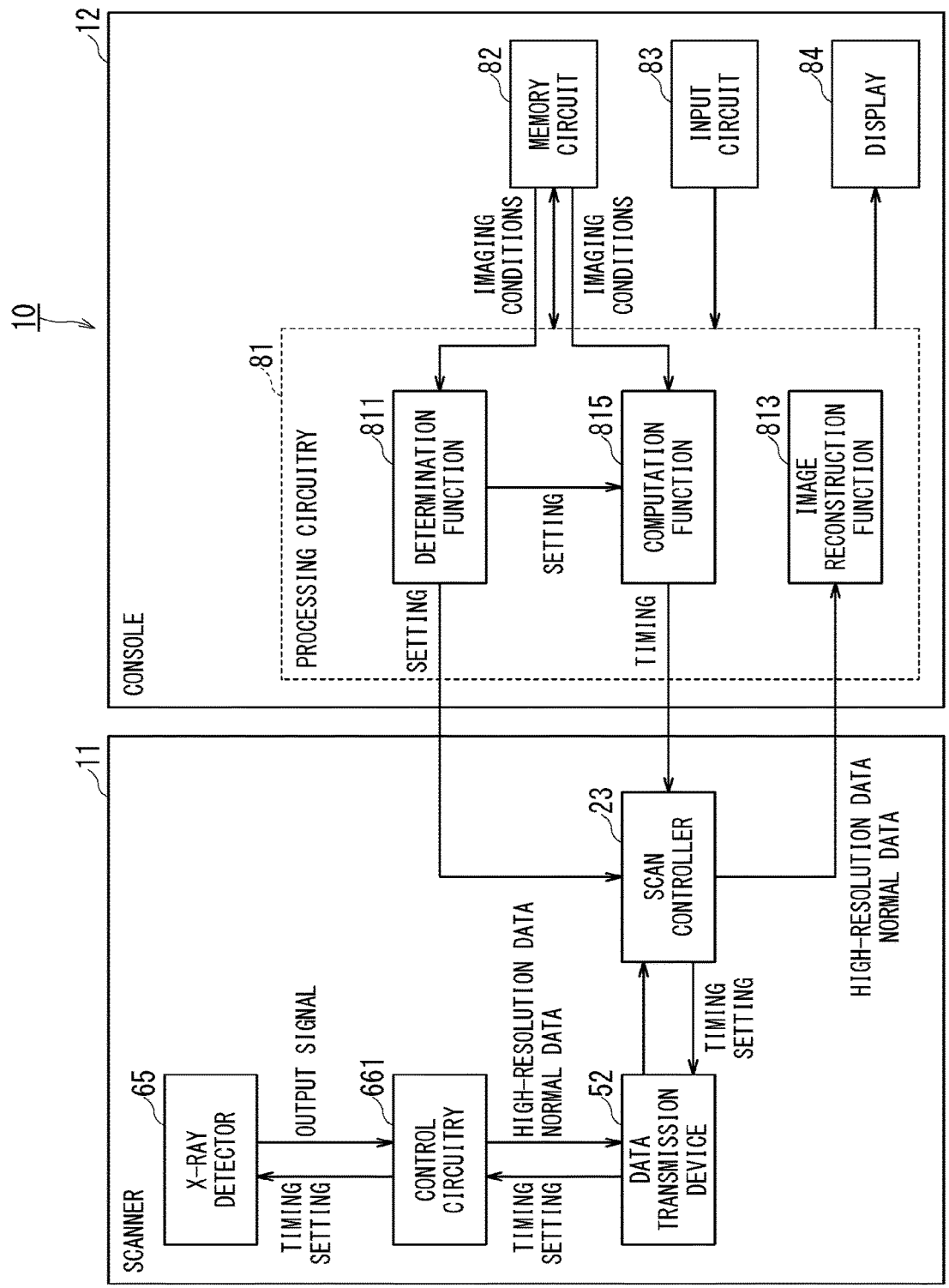
FIG. 20 is a functional block diagram illustrating configuration of the X-ray CT apparatus in the third embodiment.

FIG. 20 is a functional block diagram illustrating configuration of the X-ray CT apparatus 10 in the third embodiment. In FIG. 20, the processing circuitry 81 of the X-ray CT apparatus 10 in the third embodiment further includes a computation function 815 in addition to the respective functions of the processing circuitry 81 of the X-ray CT apparatus 10 in the second embodiment shown in FIG. 18. The computation function 815 is a function which the processor of the processing circuitry 81 implements by executing the corresponding program stored in the memory circuit 82.

The determination function 811 determines setting of detection elements on the basis of the imaging conditions stored in the memory circuit 82. The imaging conditions include, e.g., an anatomical imaging part, and the determination function 811 determines which of the high-resolution setting and the normal setting is applied, for each anatomical imaging part.

The computation function 815 computes a timing of controlling the high-resolution setting and the normal setting, depending on the anatomical imaging part included in the imaging conditions which are stored in the memory circuit 82. In other words, the computation function 815 computes which view includes the target anatomical imaging part, on the basis of imaging conditions, and then computes a timing at which setting of detection elements is switched. The imaging conditions includes, e.g., an imaging position, a standard size of each anatomical imaging part, a position of the table 71, a posture of the object Q, a position on the table 71 on which the object Q is mounted, an angle of view, rotation time, a total scan time, and slice thickness. The imaging conditions further includes, e.g., the current position of the table 71 and movement amount of the table 71 which are acquired from the table controller 72. On the basis of such information on the imaging conditions, the computation function 815 computes the timing at which setting of detection elements is switched.

Figures 21, 22:
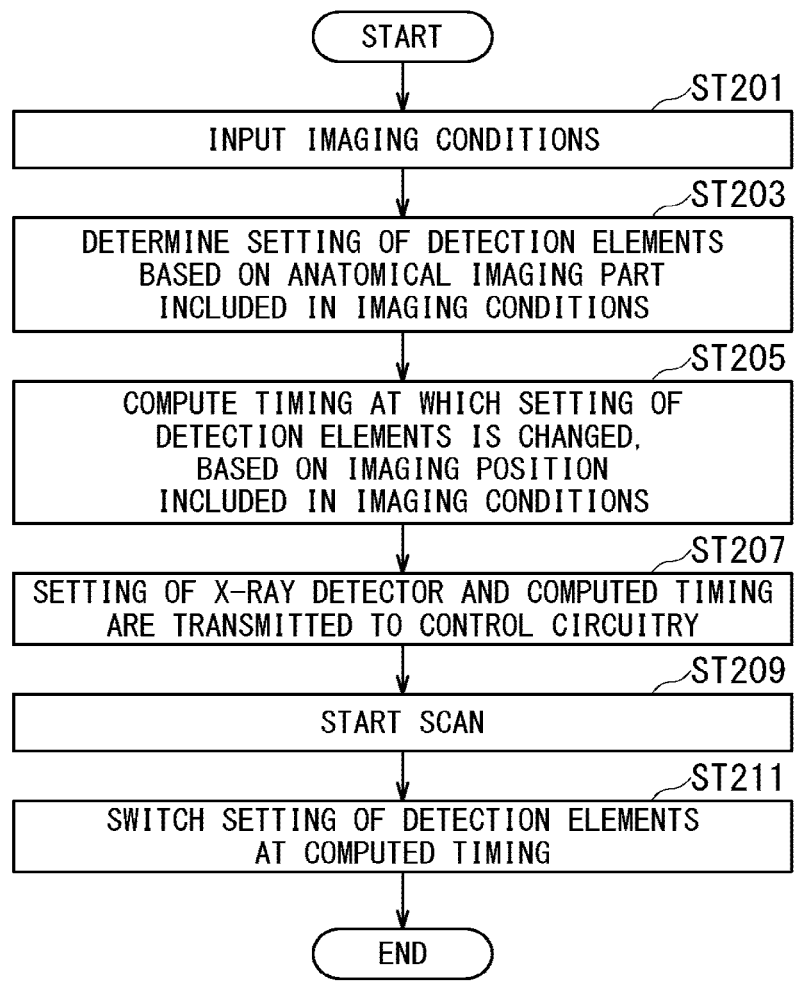
FIG. 21 is a flowchart illustrating an operation performed by the X-ray CT apparatus of the third embodiment.
FIG. 22 is a table illustrating setting of detection elements for each anatomical imaging part in the third embodiment.

FIG. 21 is a flowchart illustrating an operation performed by the X-ray CT apparatus 10 of the third embodiment. Hereinafter, the operation of the X-ray CT apparatus 10 in the third embodiment will be described according to the step number in the flowchart of FIG. 21 by referring to FIG. 22 and FIG. 23 as required.

In the step ST201, imaging conditions are inputted to the X-ray CT apparatus 10. The inputted imaging conditions are stored in the memory circuit 82. Note that the imaging conditions may be stored in the memory circuit 82 in advance of input. Additionally, for instance, the imaging conditions may be stored in an external memory device and be inputted to the memory circuit 82 of the X-ray CT apparatus 10 via an electronic network or be inputted by a user via the input circuit 83.

In the next step ST 203, the determination function 811 determines setting of detection elements on the basis of an anatomical imaging part included in the imaging conditions. Setting of detection elements is performed by the determination function 811 for each anatomical imaging part, and its details will be described below by referring to FIG. 22 and FIG. 23.

FIG. 22 is a table (i.e., a list) illustrating setting of detection elements for each anatomical imaging part in the third embodiment. FIG. 22 is a list which indicates setting of detection elements for each anatomical imaging part. The table of FIG. 22 shows the high-resolution setting for a head, the normal setting for the chest, the normal setting for an abdomen, . . . , the normal setting for lower limbs, from the top. Since the high-resolution setting provides higher resolution, it is preferable to acquire image data under the high-resolution setting from an anatomical imaging part of involving a minute structure such as a head, as shown in the table of FIG. 22. Contrastively, as to an anatomical imaging part where X-ray signal intensity is more important than resolution such as an abdomen, it is preferable to acquire image data under the normal setting which provides a satisfactory S/N ratio. Additionally, when quantitative observation such as measurement of blood volume is performed, it is preferable to acquire an image with a satisfactory S/N ratio. As described above, image quality required for image data to be acquired differ depending on various conditions such as its anatomical imaging part and a type of examination.

Figure 23:
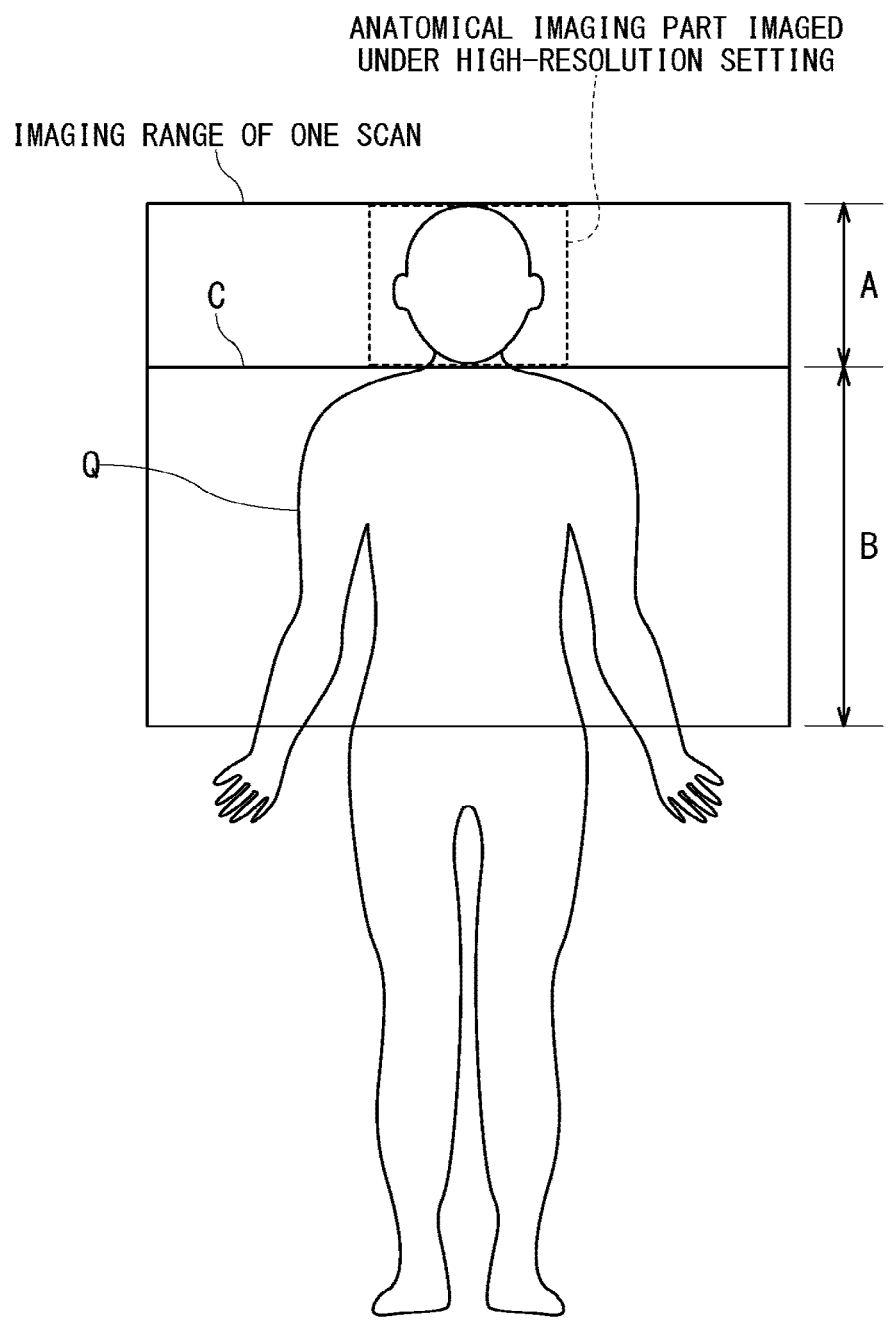
FIG. 23 is a schematic diagram illustrating switching of setting of detection elements for each anatomical imaging part in the third embodiment.

FIG. 23 is a schematic diagram illustrating a case where a head, a chest, and an abdomen are included in the imaging range and are imaged in one scan. As described in the table of FIG. 22, the head is an anatomical imaging part from which image data are preferably acquired under the high-resolution setting. The chest and the abdomen are anatomical imaging parts from which image data are preferably acquired under the normal setting. The arrow A in FIG. 23 indicates the range which should be imaged under the high-resolution setting, and the arrow B in FIG. 23 indicates the range which should be imaged under the normal setting. As described above, setting of detection elements is changed at the border position indicated by the straight line C depending on the imaging conditions.

Returning to FIG. 21, the description of the flowchart is continued.

In the next step ST205, the computation function 815 computes the timing at which setting of detection elements is changed, on the basis of the imaging conditions. The computation function 815 computes the imaging time and/or view number until reaching the timing at which setting of detection elements is changed, on the basis of the imaging position, the standard size of the anatomical imaging part, the position on the table 71 on which the object Q is mounted, an angle of view, and rotation time included in the imaging conditions.

In the next step ST207, the control circuitry 661 receives the setting of the X-ray detector 65 determined by the determination function 811 and the timing computed by the computation function 815 from the processing circuitry 81 via the scan controller 23.

In the next step ST209, the scanner 11 starts a scan on the basis of the imaging conditions.

In the next step ST211, the control circuitry 661 switches setting of detection elements at the timing computed by the computation function 815. Additionally, at least one of the arrangement patterns described in FIG. 10 to FIG. 12 may be applied to the range which is determined to be set to the high-resolution setting in the X-ray detector 65, in a manner similar to the second embodiment.

Further, each anatomical imaging part may be set not by unit of apparent body region such as a head and a chest but by unit of internal organ such as a heart and a brain. Moreover, setting of the X-ray detector 65 may be performed depending on which region receives X-rays having passed through the target region. In other words, when cardiac image data are acquired under the high-resolution setting, the X-ray CT apparatus 10 may apply the high-resolution setting to the region of detection elements, which receive X-rays having passed through the heart, in the X-ray detector 65.

Furthermore, the X-ray CT apparatus 10 may be configured such that a user can input both of a range to be set to the high-resolution setting and a range to be set to the normal setting via the input circuit 83, in the case of determining the imaging range on the basis of a scanogram image.

As described above, when image data of plural anatomical imaging parts are acquired in one scan, the X-ray CT apparatus 10 of the third embodiment can dynamically control setting of detection elements depending on each anatomical imaging part so as to acquire image data with resolution and S/N ratios which are appropriate for the respective anatomical imaging parts.

According to the X-ray CT apparatus 10 and the X-ray detection device 20 of at least one of the above-described embodiments, it is possible to acquire high-resolution data and normal data in one scan.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
an X-ray detector equipped with a plurality of detection elements each of which is configured to output an X-ray signal in accordance with X-rays passing through an object; and
a scan controller configured to acquire X-ray signals in each of a first mode and a second mode during a same scan by switching between the first mode and the second mode during the same scan without changing a size of an X-ray irradiation area on the X-ray detector,
wherein, in the first mode, the scan controller acquires each X-ray signal outputted from each of the plurality of detection elements as high-resolution data, and in the second mode, the scan controller integrates X-ray signals outputted from some of the plurality of detection elements and acquires the integrated X-ray signals as normal-resolution data.

2. The X-ray CT apparatus according to claim 1,
wherein the X-ray detector includes an arrangement region where the plurality of detection elements are arranged; and
a part of the arrangement region is set to a high-resolution region for acquiring the high-resolution data and rest of the arrangement region is set to a normal-resolution region for acquiring the normal-resolution data.

3. The X-ray CT apparatus according to claim 1,
wherein the X-ray detector includes an arrangement region where the plurality of detection elements are arranged; and
entirety of the arrangement region is set to a high-resolution region from which the high-resolution data can be acquired.

4. The X-ray CT apparatus according to claim 2,
wherein the plurality of detection elements are arrayed in columns in a column direction and in rows in a channel direction; and
the scan controller is configured to set a scan mode to each of the plurality of detection elements in such a manner that the scan mode is unified between detection elements of each column but differs between detection elements of each row.

5. The X-ray CT apparatus according to claim 2,
wherein the plurality of detection elements are arrayed in columns in a column direction and in rows in a channel direction; and
the scan controller is configured to set a scan mode to each of the plurality of detection elements in such a manner that the scan mode is unified between detection elements of each row but differs between detection elements of each column.

6. The X-ray CT apparatus according to claim 2,
wherein the plurality of detection elements are arrayed in columns in a column direction and in rows in a channel direction; and
the scan controller is configured to set a scan mode to each of the plurality of detection elements in such a manner that the scan mode differs between detection elements of each row and differs between detection elements of each column.

7. The X-ray CT apparatus according to claim 3,
wherein the plurality of detection elements are arrayed in columns in a column direction and in rows in a channel direction; and
the scan controller is configured to set a scan mode to each of the plurality of detection elements in such a manner that the scan mode is unified between detection elements of each column but differs between detection elements of each row.

8. The X-ray CT apparatus according to claim 3,
wherein the plurality of detection elements are arrayed in columns in a column direction and in rows in a channel direction; and
the scan controller is configured to set a scan mode to each of the plurality of detection elements in such a manner that the scan mode is unified between detection elements of each row but differs between detection elements of each column.

9. The X-ray CT apparatus according to claim 3,
wherein the plurality of detection elements are arrayed in columns in a column direction and in rows in a channel direction; and
the scan controller is configured to set a scan mode to each of the plurality of detection elements in such a manner that the scan mode differs between detection elements of each row and differs between detection elements of each column.

10. The X-ray CT apparatus according to claim 4,
wherein the scan controller is configured to acquire the high-resolution data and the normal-resolution data by switching between the first mode and the second mode for each of the plurality of detection elements depending on a view, in one scan in which X-ray signals are acquired at respective views.

11. The X-ray CT apparatus according to claim 5, wherein the scan controller is configured to acquire the high-resolution data and the normal-resolution data by switching between the first mode and the second mode for each of the plurality of detection elements depending on a view, in one scan in which X-ray signals are acquired at respective views.

12. The X-ray CT apparatus according to claim 6, wherein the scan controller is configured to acquire the high-resolution data and the normal-resolution data by switching between the first mode and the second mode for each of the plurality of detection elements depending on a view, in one scan in which X-ray signals are acquired at respective views.

13. The X-ray CT apparatus according to claim 7, wherein the scan controller is configured to acquire the high-resolution data and the normal-resolution data by switching between the first mode and the second mode for each of the plurality of detection elements depending on a view, in one scan in which X-ray signals are acquired at respective views.

14. The X-ray CT apparatus according to claim 8, wherein the scan controller is configured to acquire the high-resolution data and the normal-resolution data by switching between the first mode and the second mode for each of the plurality of detection elements depending on a view, in one scan in which X-ray signals are acquired at respective views.

15. The X-ray CT apparatus according to claim 9, wherein the scan controller is configured to acquire the high-resolution data and the normal-resolution data by switching between the first mode and the second mode for each of the plurality of detection elements depending on a view, in one scan in which X-ray signals are acquired at respective views.

16. The X-ray CT apparatus according to claim 1, wherein the scan controller is configured to switch between the first mode and the second mode for each of the plurality of detection elements, depending on X-ray signal intensity acquired by the X-ray detector.

17. The X-ray CT apparatus according to claim 1, further comprising:
a memory circuit configured to store an imaging condition; and
processing circuitry configured to compute a timing at which the first mode and the second mode are switched, based on the imaging condition,
wherein the scan controller is configured to switch between the first mode and the second mode based on the timing computed by the processing circuitry.

18. An X-ray detection device comprising:
a plurality of detection elements each of which is configured to detect X-rays and output an X-ray signal; and
a data acquisition circuit configured to acquire X-ray signals in each of a first mode and a second mode during a same scan by switching between the first mode and the second mode during the same scan without changing a size of an X-ray irradiation area on the X-ray detection device,
wherein, in the first mode, a scan controller acquires each X-ray signal outputted from each of the plurality of detection elements as high-resolution data, and in the second mode, the scan controller integrates X-ray signals outputted from some of the plurality of detection elements and acquires the integrated X-ray signals as normal-resolution data.

* * * * *